US008895919B2

(12) United States Patent
Nishino

(10) Patent No.: US 8,895,919 B2
(45) Date of Patent: Nov. 25, 2014

(54) ION GENERATING APPARATUS AND JUDGMENT METHOD FOR PRESENCE OR ABSENCE OF IONS

(75) Inventor: Masafumi Nishino, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 676 days.

(21) Appl. No.: 13/259,373

(22) PCT Filed: Jan. 26, 2010

(86) PCT No.: PCT/JP2010/050980

§ 371 (c)(1), (2), (4) Date: Sep. 23, 2011

(87) PCT Pub. No.: WO2010/109940

PCT Pub. Date: Sep. 30, 2010

(65) Prior Publication Data

US 2012/0006996 A1 Jan. 12, 2012

(30) Foreign Application Priority Data

Mar. 25, 2009 (JP) ................................ 2009-074607

(51) Int. Cl.
*H01T 23/00* (2006.01)
*A61L 9/22* (2006.01)

(52) U.S. Cl.
CPC .. *H01T 23/00* (2013.01); *A61L 9/22* (2013.01)
USPC ........................ 250/285; 250/423 R; 250/424

(58) Field of Classification Search
USPC ...................... 250/281, 282, 285, 423 R, 424
See application file for complete search history.

(56) References Cited

U.S. PATENT DOCUMENTS

2007/0109711 A1 5/2007 Sekoguchi et al.

FOREIGN PATENT DOCUMENTS

| | | | |
|---|---|---|---|
| JP | 4-164804 | A | 6/1992 |
| JP | 6-68398 | U | 9/1994 |
| JP | 2003-336872 | A | 11/2003 |
| JP | 2004-3885 | A | 1/2004 |
| JP | 2004-363088 | A | 12/2004 |
| JP | 2005-328904 | A | 12/2005 |
| JP | 2007-114177 | A | 5/2007 |
| JP | 2008-16274 | A | 1/2008 |
| JP | 2010-54371 | A | 3/2010 |
| JP | 2010-92773 | A | 4/2010 |

OTHER PUBLICATIONS

International Search Report (PCT/ISA/210) dated Apr. 13, 2010 for PCT/JP2010/050980.

*Primary Examiner* — Mark R Gaworecki
(74) *Attorney, Agent, or Firm* — Birch, Stewart, Kolasch & Birch, LLP

(57) ABSTRACT

A measuring part 67 measures the potential of a collecting electrode 66 having collected positive and negative ions respectively generated by ion generating parts 61 of ion generators *6a* and *6b* and ion generating parts 62 of ion generators *6c* and *6d*. In the judgment of the presence or absence of ions, the ion generators *6a* and *6b* and the ion generators *6c* and *6d* are alternately turned ON/OFF. In ion judgment 1, ON/OFF is performed 6 times with a period of 10 seconds. In ion judgment 2, ON/OFF is performed 10 times with a period of 1 second. Then, when the difference (the amount of change) between the maximum value and the minimum value of the output voltage of the measuring part 67 is greater than a given threshold value, the presence of ions is concluded respectively.

12 Claims, 19 Drawing Sheets

F I G. 3
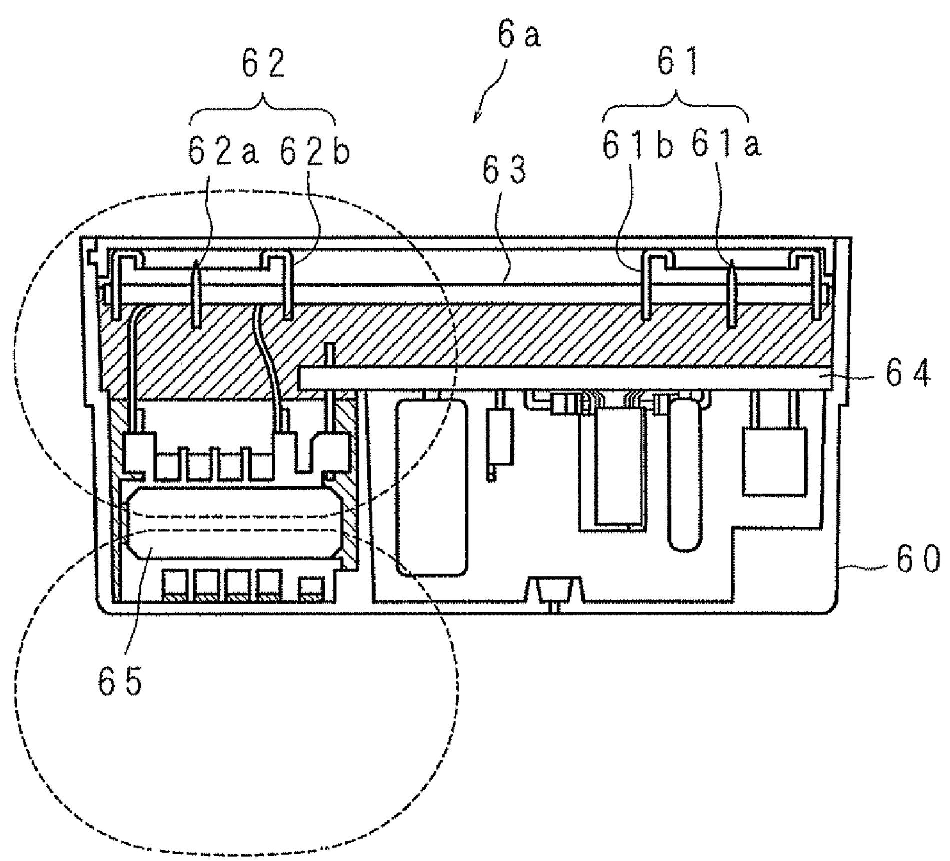

F I G. 4
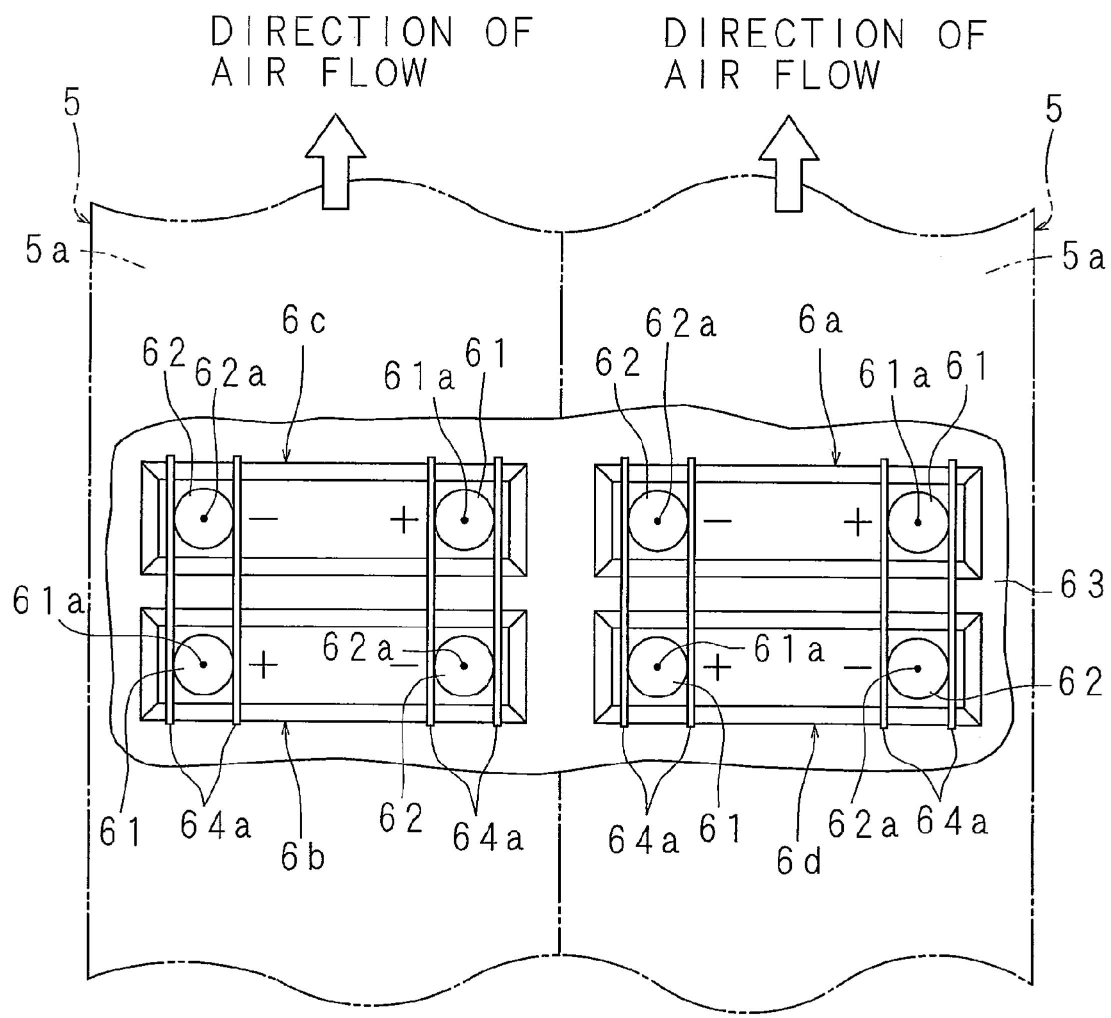

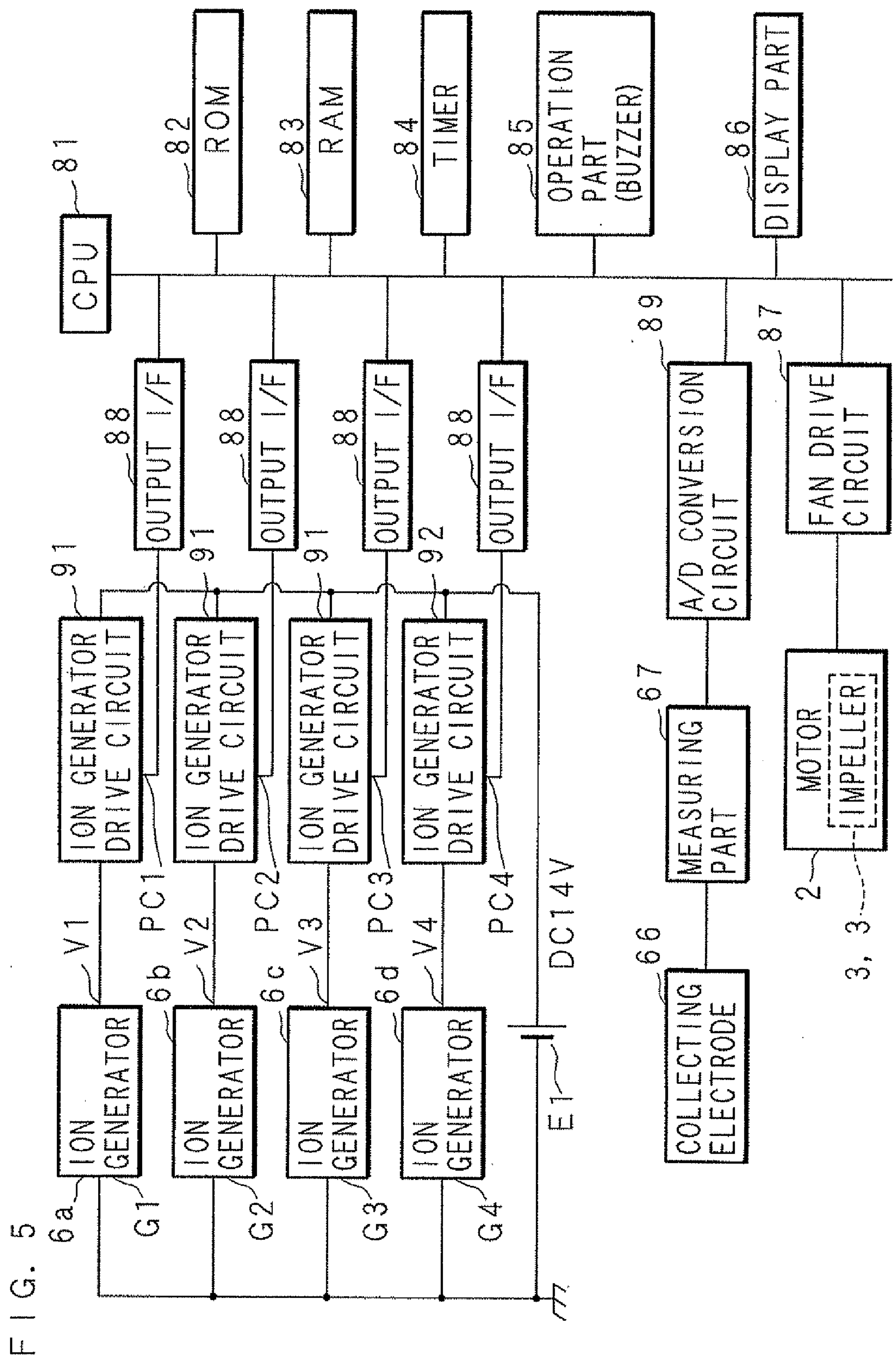
F I G. 5
CPU
81
ROM
82
RAM
83
TIMER
84
OPERATION PART (BUZZER)
85
DISPLAY PART
86
OUTPUT I/F
88
A/D CONVERSION CIRCUIT
89
FAN DRIVE CIRCUIT
87
ION GENERATOR DRIVE CIRCUIT
91
92
ION GENERATOR
6a
6b
6c
6d
V1
V2
V3
V4
G1
G2
G3
G4
PC1
PC2
PC3
PC4
DC14V
E1
MEASURING PART
67
COLLECTING ELECTRODE
66
MOTOR
IMPELLER
2
3, 3

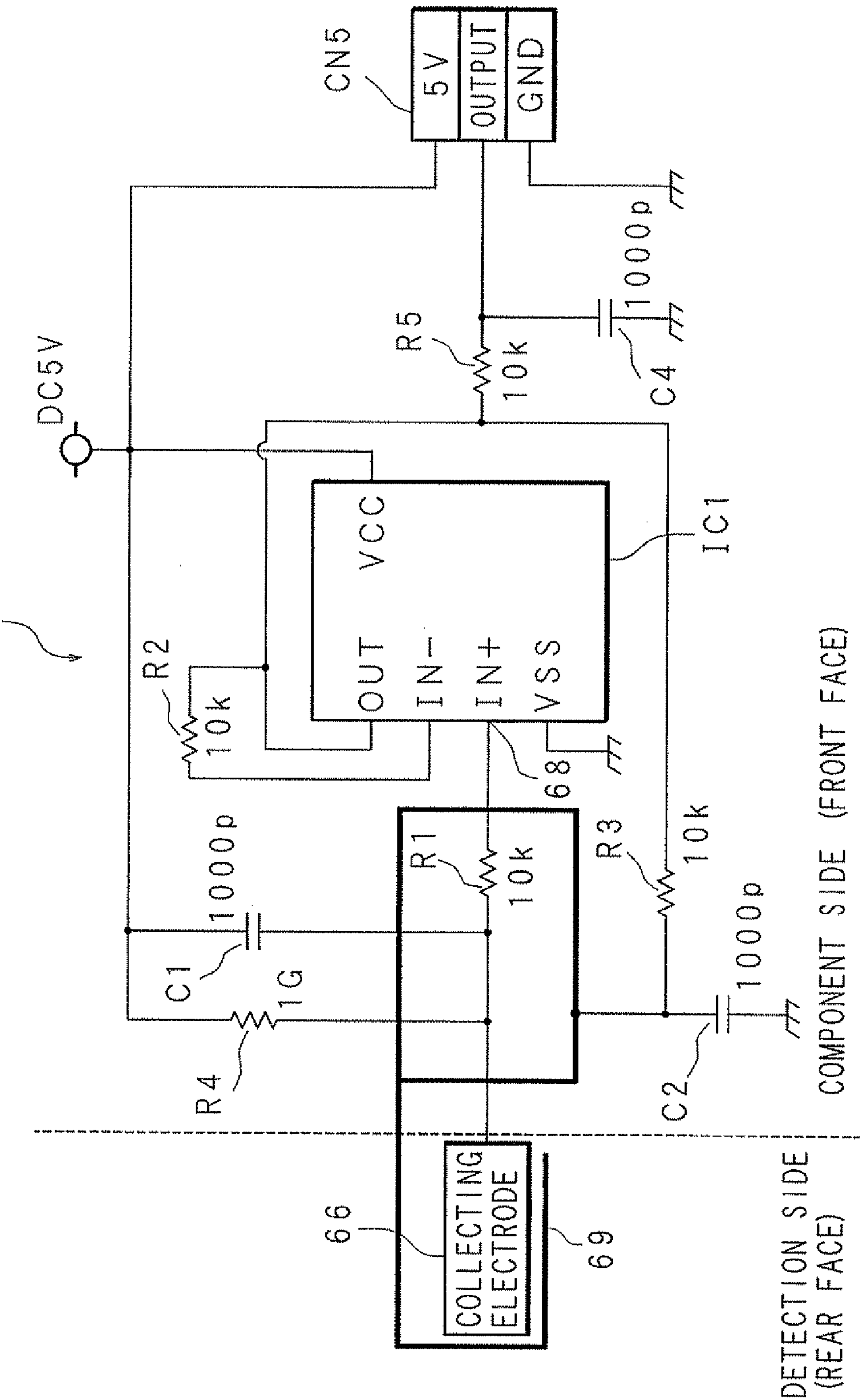
F I G. 7
67
CN5
5 V
OUTPUT
GND
DC5V
R5
10k
C4
1000p
VCC
OUT
IN−
IN+
VSS
IC1
R2
10k
68
R1
10k
R3
10k
C1
1000p
R4
1G
C2
1000p
COMPONENT SIDE (FRONT FACE)
66
COLLECTING ELECTRODE
69
DETECTION SIDE (REAR FACE)

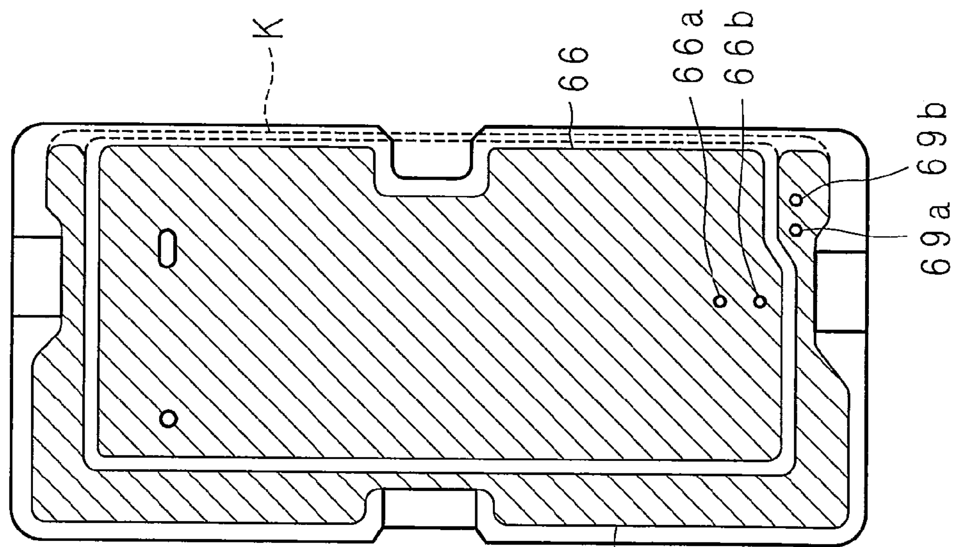
F I G. 8 B
K
66
66a
66b
69b
69a
69
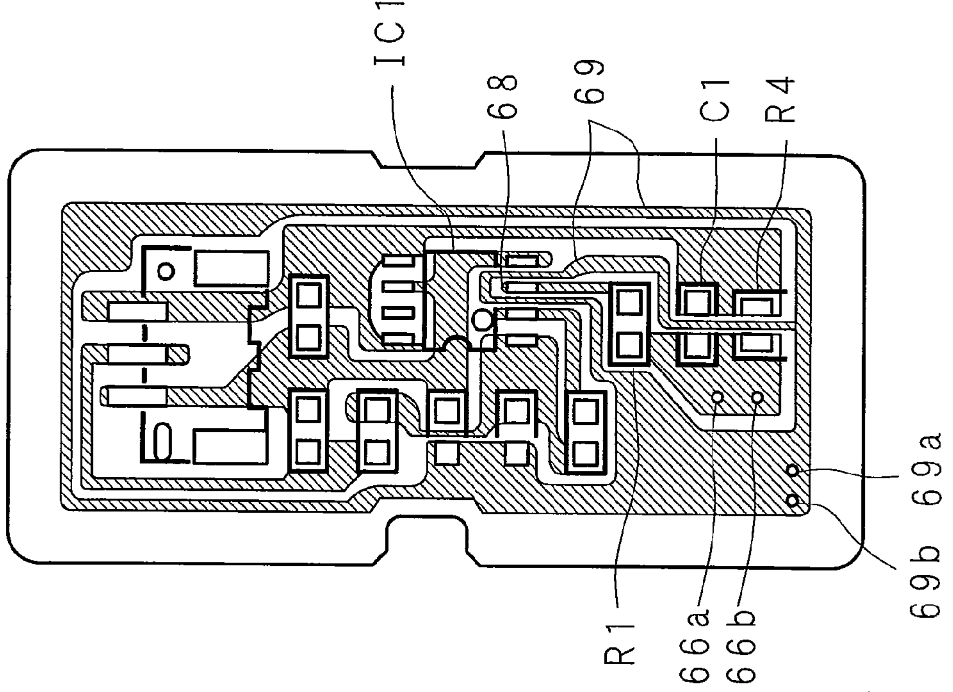
F I G. 8 A
IC1
68
69
C1
R4
69a
69b
R1
66a
66b

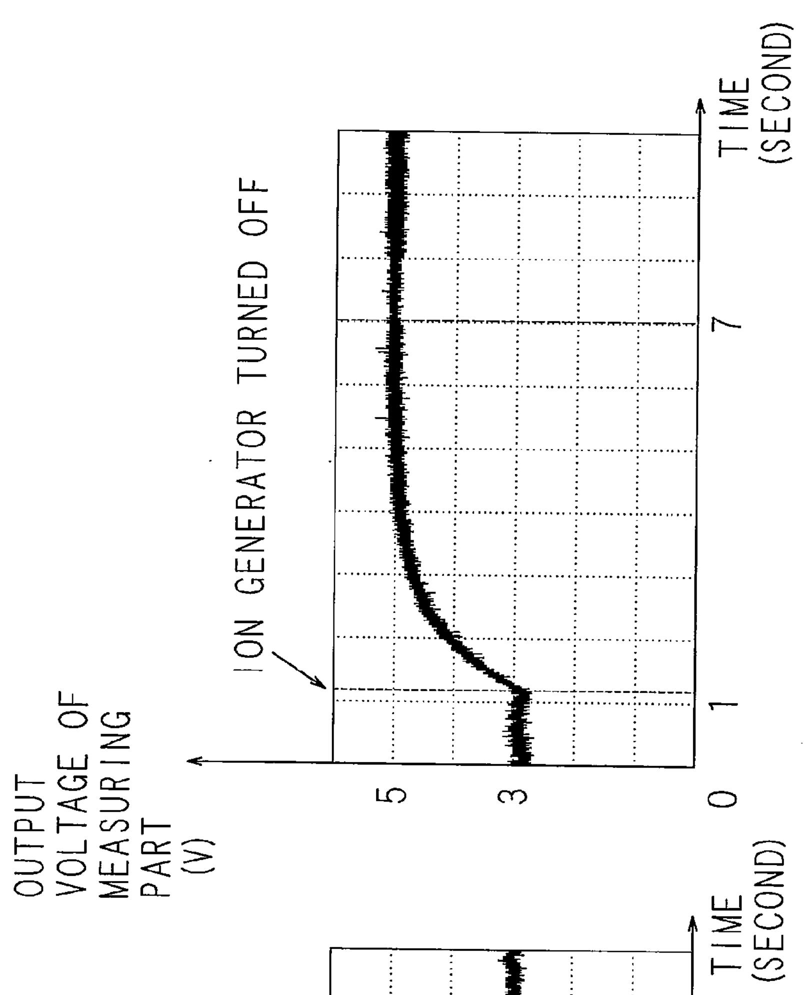
F I G. 1 0 A
F I G. 1 0 B

F I G. 1 1
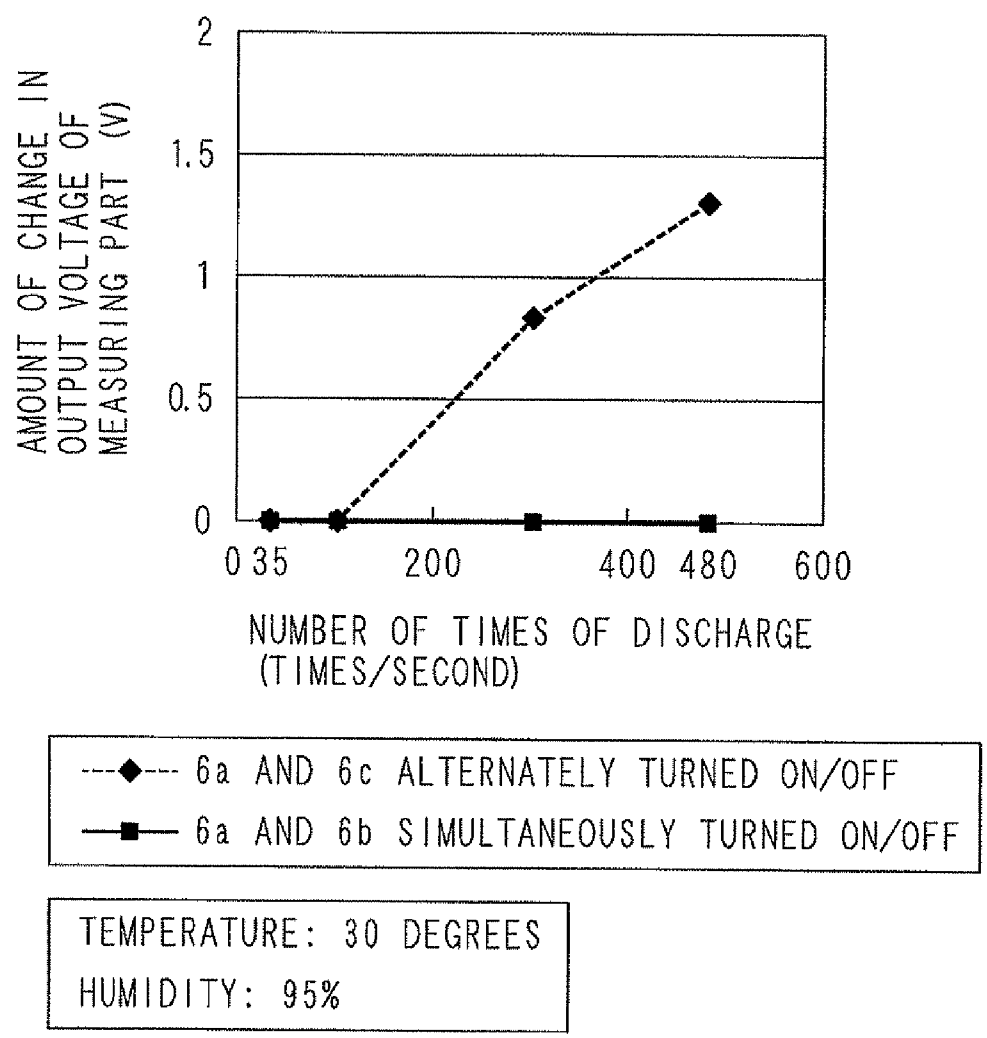

NUMBER OF TIMES OF DISCHARGE
: 480 TIMES/SECOND

F I G. 15
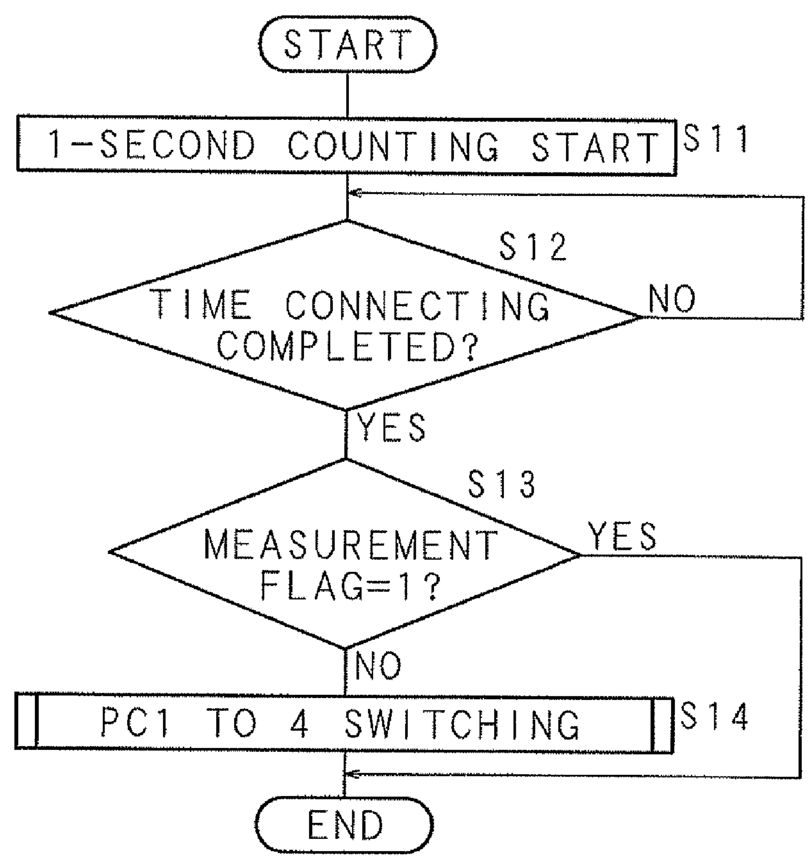

F I G. 16
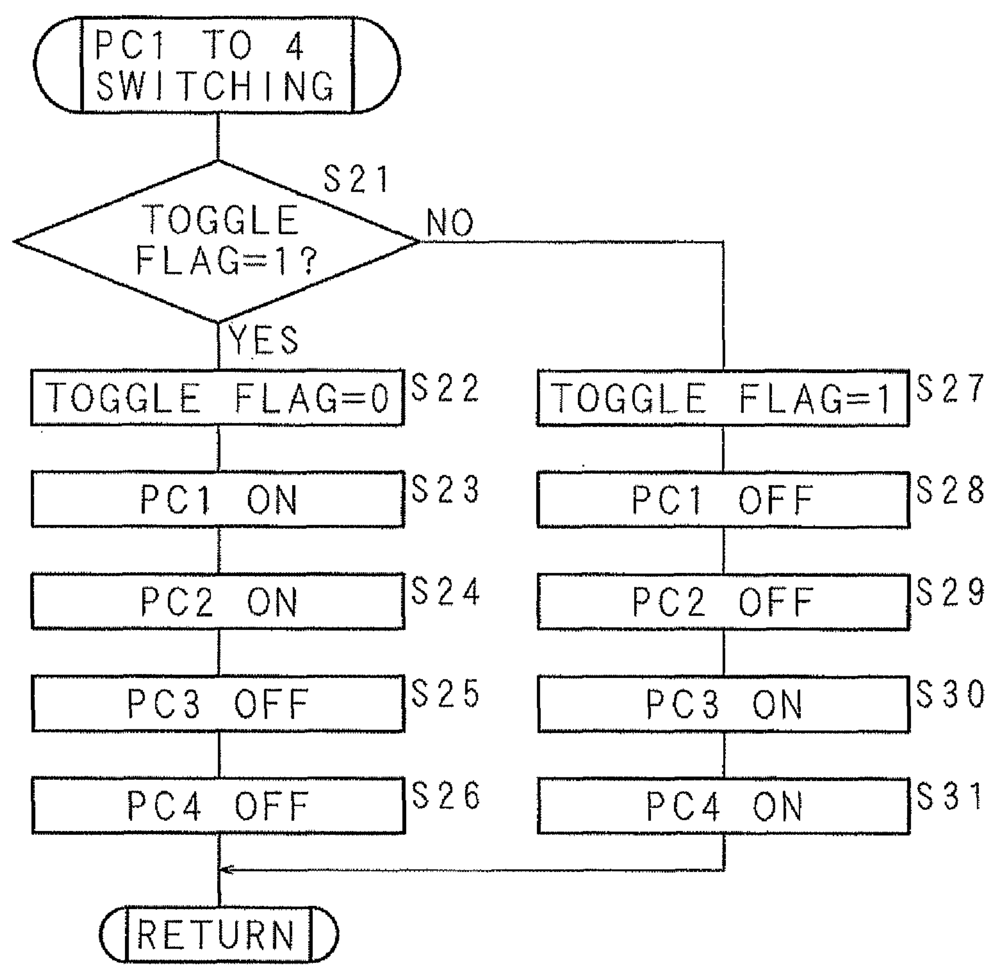

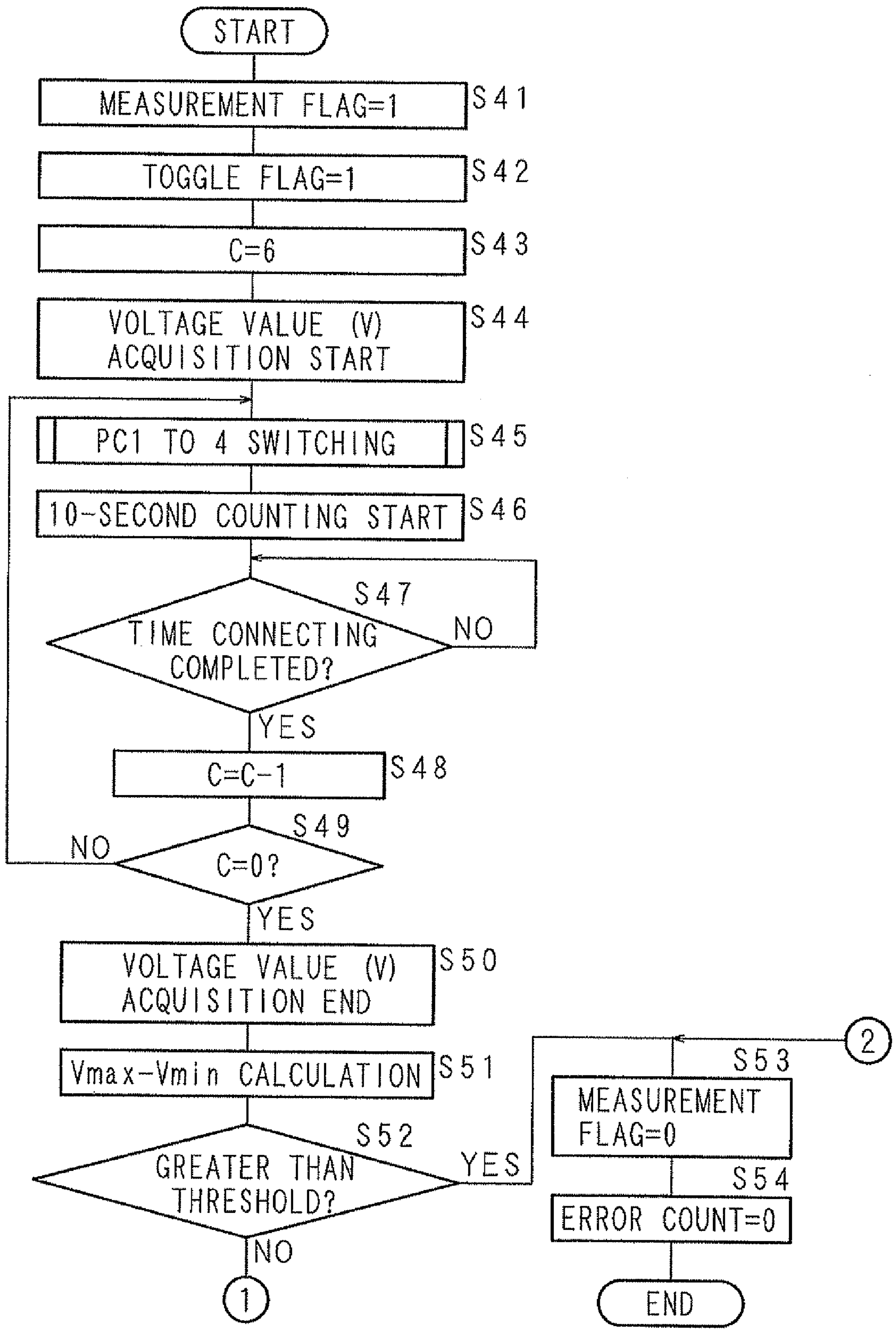
F I G. 1 7
START
MEASUREMENT FLAG=1
S41
TOGGLE FLAG=1
S42
C=6
S43
VOLTAGE VALUE (V) ACQUISITION START
S44
PC1 TO 4 SWITCHING
S45
10-SECOND COUNTING START
S46
S47
TIME CONNECTING COMPLETED?
NO
YES
C=C-1
S48
S49
NO
C=0?
YES
VOLTAGE VALUE (V) ACQUISITION END
S50
Vmax-Vmin CALCULATION
S51
S52
GREATER THAN THRESHOLD?
YES
NO
1
2
S53
MEASUREMENT FLAG=0
S54
ERROR COUNT=0
END

ION GENERATING APPARATUS AND JUDGMENT METHOD FOR PRESENCE OR ABSENCE OF IONS

This application is the national phase under 35 U.S.C. §371 of PCT International Application No. PCT/JP2010/050980 which has an International filing date of, Jan. 26, 2010 and designated the United States of America

BACKGROUND

1. Field of the Invention

The present invention relates to: an ion generating apparatus provided with an ion detector for detecting ions in air; and a judgment method for presence or absence of ions.

2. Description of the Related Art

In recent years, techniques for cleaning air in a residential space by virtue of positive and/or negative ions are used widely. For example, in ion generating apparatuses including air cleaners, an ion generator generating positive and negative ions is arranged in the middle of the internal ventilation flue. Then, the generated ions are released to the external space together with air.

In a space where ions have been released, when the concentration of ions is 1,000 to 2,000 ions/$cm^3$ or the like, a significant disinfection effect is obtained against bacteria such as serratia bacteria and bacillus bacteria. Further, ions in air inactivate airborne particles and denature odor components. Thus, air is cleaned in the entire residential space.

In standard ion generators providing the above-mentioned effect, a driving voltage of high-voltage alternating current is applied between a needle electrode and an opposite electrodes or alternatively between a discharge electrode and a dielectric electrode so that corona discharge is generated and hence positive and negative ions is generated. When a plurality of ion generators are employed, the concentration of ions in air is enhanced.

On the other hand, during long term operation of ion generators, the discharge electrode is worn out by spatter evaporation associated with corona discharge or alternatively the foreign substances such as chemical substances and dust are adhered to and accumulated on the discharge electrode. In such cases, the rate of ion generation decreases unavoidably. Then, in order that the user should be notified that maintenance is necessary for the ion generator, the presence or absence of ions in air need be judged.

In such a situation, for example, Japanese Patent Application Laid-Open No. 2007-114177 (Patent Document 1, hereinafter) discloses an ion detecting device and an ion generating apparatus in which a collecting electrode collecting ions in air is provided and the presence or absence of ions is detected (judged) on the basis of a change in the potential of the collecting electrode generated when ion generating operation is started (or when ion generating operation is stopped).

SUMMARY

Meanwhile, as described above, in the conventional art, the fact has been known that $H^+(H_2O)_m$ (m is an arbitrary natural number) which is a positive ion and $O_2^-(H_2O)_n$ (n is an arbitrary natural number) which is a negative ion sterilize floating bacteria and the like in air by means of reactions with the ions. Nevertheless, these ions recombine and disappear with each other. Thus, even when a high concentration is realized near the electrode of the ion generator, the concentration decreases rapidly with increasing distance from the ion generator. Thus, although an ion concentration of a few tens of thousands of ions/$cm^3$ is achievable in a space of small volume like in an experiment apparatus, the ion concentration has been limited to at most 2,000 to 3,000 ions/$cm^3$ in a space of large volume like an actual residential space and a workspace.

On the other hand, the present inventors have found that at laboratory levels, the ions concentration of 7,000 ions/$cm^3$ eliminates 99% of bird influenza viruses in 10 minutes and the ions concentration of 50,000 ions/$cm^3$ eliminates up to 99.9%. These elimination factors indicate that when 1,000 viruses/$cm^3$ are initially present in air, 10 viruses/$cm^3$ and 1 virus/$cm^3$ remain respectively. In other words, when the ion concentration is increased from 7,000 ions/$cm^3$ to 50,000 ions/$cm^3$, the remained viruses decrease into 1/10.

As such, a finding has been obtained that from the perspective of infection prevention and environmental clean-up, it is extremely important that a high ion concentration is maintained in the entirety of the residential space and the workspace where people and the like live.

Nevertheless, when air under judgment of ion concentration and the presence or absence of ions is at a high temperature and a high humidity, the amount of change in the potential is small. Thus, the technique disclosed in Patent Document 1 has a problem that even the judgment of the presence or absence of ions is difficult. Further, after the ion generator has been operated for a long time, the generated ions themselves decrease. Thus, the amount of change in the potential becomes yet smaller, and hence judgment of the presence or absence of ions becomes more difficult.

The present invention has been devised in view of this situation. An object of the present invention is to provide an ion generating apparatus and a judgment method for presence or absence of ions in which the presence or absence of ions is judged with precision free from the influence of temperature and humidity and the influence of time dependent change in the ion generator.

Means for Solving the Problem

The ion generating apparatus according to the present invention is an ion generating apparatus in which a plurality of ion generators generate positive and negative ions and which comprises: a drive circuit turning ON/OFF the ion generators; an ion detector detecting an index indicating a state of generation of the ions generated by the ion generators; and judging means for judging presence or absence of the ions on the basis of the index detected by the ion detector, wherein in a case that the drive circuit turns ON one ion generator and the other ion generator periodically at different timings, when a difference of the indices detected by the ions detector is greater than a given threshold value, the judging means concludes presence of the ions.

In the present invention, in a case that the individual ion generators are turned ON at one or a plurality of different timings, when the difference of the indices indicating the state of generation of ions is greater (or smaller) than a given threshold value, the presence (or the absence) of ions is concluded.

Thus, in a case that the ion generators respectively generating positive and negative ions are turned ON at different timings, the difference in the index detected when the individual ion generators are turned ON increases in comparison with the amount of change in the index detected when one ion generator is turned ON/OFF. Thus, judgment of the presence or absence of ions becomes easy.

Thus, like in a case that air under the judgment of the presence or absence of ions is at a high temperature and a high humidity or in a case that the rate of ion generation has decreased owing to a time dependent change of the ion generators, even in a case that the amount of change in the index associated with the ON/OFF of one ion generator is small and hence judgment of the presence or absence of ions is difficult, judgment of the presence or absence of ions is achieved without errors.

The ion generating apparatus according to the present invention is characterized in that in the one ion generator and the other ion generator, positive and negative ion generating parts are installed in parallel in each ion generator, the directions of parallel installation of the individual ion generating parts are aligned, and the ion generators are biased such that the ion generating parts do not overlap in the direction of parallel installation.

In the present invention, ion generators in which the directions of parallel installation of positive and negative ion generating parts are aligned are biased such that the ion generating parts do not overlap in the direction of parallel installation.

Thus, in a case that the ion generators are arranged in the ventilation flue such that the direction of parallel installation is approximately at right angles to the air flow running near each ion generating part and then the index is detected on the basis of the ions generated respectively by the positive ion generating part of one ion generator and the negative ion generating part of the other ion generator, the difference in the index detected when the individual ion generators are turned ON at different timings increases in comparison with the amount of change in the index detected when the one ion generator is turned ON/OFF. Thus, judgment of the presence or absence of ions becomes easy.

The ion generating apparatus according to the present invention is characterized in that the one ion generator and the other ion generator are installed in alignment in the direction of parallel installation, and that each ion generating part generates ions toward one side of a direction crossing perpendicularly to the direction of aligned installation.

In the present invention, the ion generators are installed in alignment in the direction of parallel installation of the ion generating parts. Further, the direction in which each ion generating part generates ions is identical and toward one side of a direction approximately perpendicular to the direction of aligned installation.

Thus, the separation distance between the ion detector and the installed in alignment ion generators is almost minimized. Accordingly, the difference in the index detected when the individual ion generators are turned ON at different timings is almost maximized and hence judgment of the presence or absence of ions is achieved reliably. Further, the ions generated in the ventilation flue by the ion generating parts are conducted efficiently together with the air flow in the ventilation flue.

The ion generating apparatus according to the present invention is characterized in that when the drive circuit turns ON the one ion generator and the other ion generator alternately with a given period, the judging means judges presence or absence of the ions.

In the present invention, the presence or absence of ions is judged in a state that the ion generators respectively generating positive and negative ions are turned ON alternately with a given period.

Thus, no overlap occurs between the ON timings in the ion generators. Accordingly, the difference in the index detected when the individual ion generators are turned ON at different timings is almost maximized and hence judgment of the presence or absence of ions is achieved reliably. Further, the judgment is performed periodically, that is, the same processing is repeated. This reduces the probability of erroneous conclusion as the absence of ions.

The ion generating apparatus according to the present invention is characterized in that in a case that the judging means has concluded absence of the ions, the judging means again judges presence or absence of the ions at the time that the drive circuit turns ON the one ion generator.

In the present invention, in a case that the absence of ions is concluded, the presence or absence of ions is judged again the time that the one ion generator is turned ON.

Thus, the presence or absence of ions is judged with focusing attention on the amount of change in the index occurring when the one ion generator is turned ON. Accordingly, the presence or absence of ions is judged by recognizing a rapid change in the index occurring when the ions are changed, for example, from positive to negative.

Thus, like in a case that the humidity of air under the judgment of the presence or absence of ions is extremely high, even in a case that the index having varied once in one direction varies in the opposite direction during the time that the ion generator is ON, the presence or absence of ions is judged without errors.

The ion generating apparatus according to the present invention is characterized by comprising means for generating a warning when the judging means has concluded absence of the ions in a given number of successive occasions.

In the present invention, when the absence of ions is concluded in a given number of successive occasions, a warning is generated to the user.

Thus, when the rate of ion generation falls, the user is notified and prompted to maintenance of the ion generators, that is, cleaning or replacement of the ion generators.

The judgment method for presence or absence of ions according to the present invention is characterized by comprising: turning ON/OFF a plurality of ion generators so as to generate positive and negative ions; detecting through an ion detector an index indicating a state of generation of the ions generated by the ion generators; and judging presence or absence of the ions on the basis of the index detected by the ion detector, wherein in a case that the ion generators respectively generating positive and negative ions are turned ON periodically at different timings, when a difference of the indices detected by the ions detector is greater than a given threshold value, presence of the ions is concluded.

In the present invention, in a case that the ion generators respectively generating positive and negative ions are turned ON at one or a plurality of different timings, when the difference of the indices indicating the state of generation of ions is greater (or smaller) than a given threshold value, the presence (or the absence) of ions is concluded.

Thus, the difference in the index detected when the individual ion generators are turned ON increases in comparison with the amount of change in the index detected when the one ion generator is turned ON/OFF. Accordingly, judgment of the presence or absence of ions becomes easy.

Effect of the Invention

According to the present invention, when the difference of the indices obtained at the time that a plurality of ion generators are turned ON/OFF is greater (or smaller) than a given threshold value, the presence (or the absence) of ions is concluded.

Thus, in a case that the ion generators respectively generating positive and negative ions are turned ON at different timings, the difference in the index detected when the individual ion generators are turned ON increases in comparison with the amount of change in the index detected when one ion generator is turned ON/OFF. Thus, judgment of the presence or absence of ions becomes easy.

Thus, like in a case that air under the judgment of the presence or absence of ions is at a high temperature and a high humidity or in a case that the rate of ion generation has decreased owing to a time dependent change of the ion generators, even in a case that the amount of change in the index associated with the ON/OFF of the ion generator is small and hence judgment of the presence or absence of ions is difficult, judgment of the presence or absence of ions is achieved without errors.

Thus, judgment of the presence or absence of ions is achieved with precision free from the influence of the temperature and the humidity and the influence of a time dependent change in the ion generators.

BRIEF DESCRIPTION OF THE DRAWINGS

FIG. 3 is a front-side sectional view illustrating a configuration of an ion generator.

FIG. 4 is a schematic elevation view in which an ion generator attached to a front wall is viewed from the inner side of a housing.

FIG. 5 is a block diagram illustrating a schematic configuration of a control system of an ion generating apparatus.

FIG. 7 is a circuit diagram illustrating a configuration of an ion detector.

FIGS. 8A and 8B are plan views illustrating a conductor pattern of a circuit board of an ion detector.

FIGS. 10A and B are graphs expressing the output voltage of a measuring part in a case that an ion generator not provided with a rib is turned ON/OFF at an ordinary temperature and an ordinary humidity.

FIG. 11 is a graph illustrating a situation that a difference in the amount of change in the output voltage of a measuring part is caused by a difference in the driving timing of an ion generator.

FIG. 15 is a flow chart illustrating a processing procedure of a CPU for driving ion generators in an ordinary operating state.

FIG. 16 is a flow chart illustrating a processing procedure of a CPU concerning a subroutine of switching of PCs 1 to 4.

FIG. 17 is a flow chart illustrating a processing procedure of a CPU for generating a warning on the basis of a result of judgment of the presence or absence of ions.

DETAILED DESCRIPTION

Hereinafter, the present invention is described below in detail with reference to the drawings illustrating an embodiment.

Figure 1:
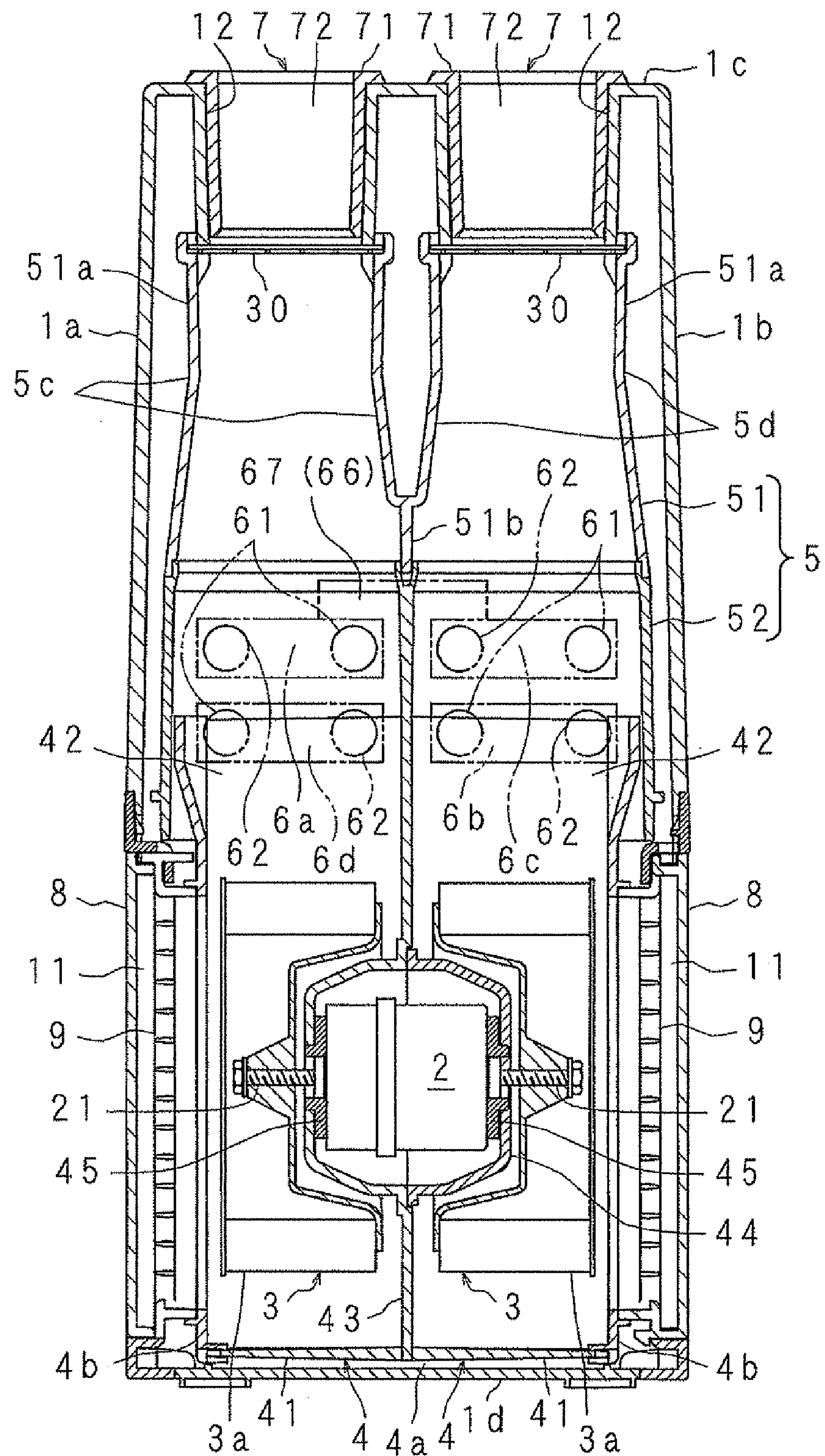
FIG. 1 is a front-side sectional view illustrating a configuration of an ion generating apparatus according to the present invention.
Figure 2:
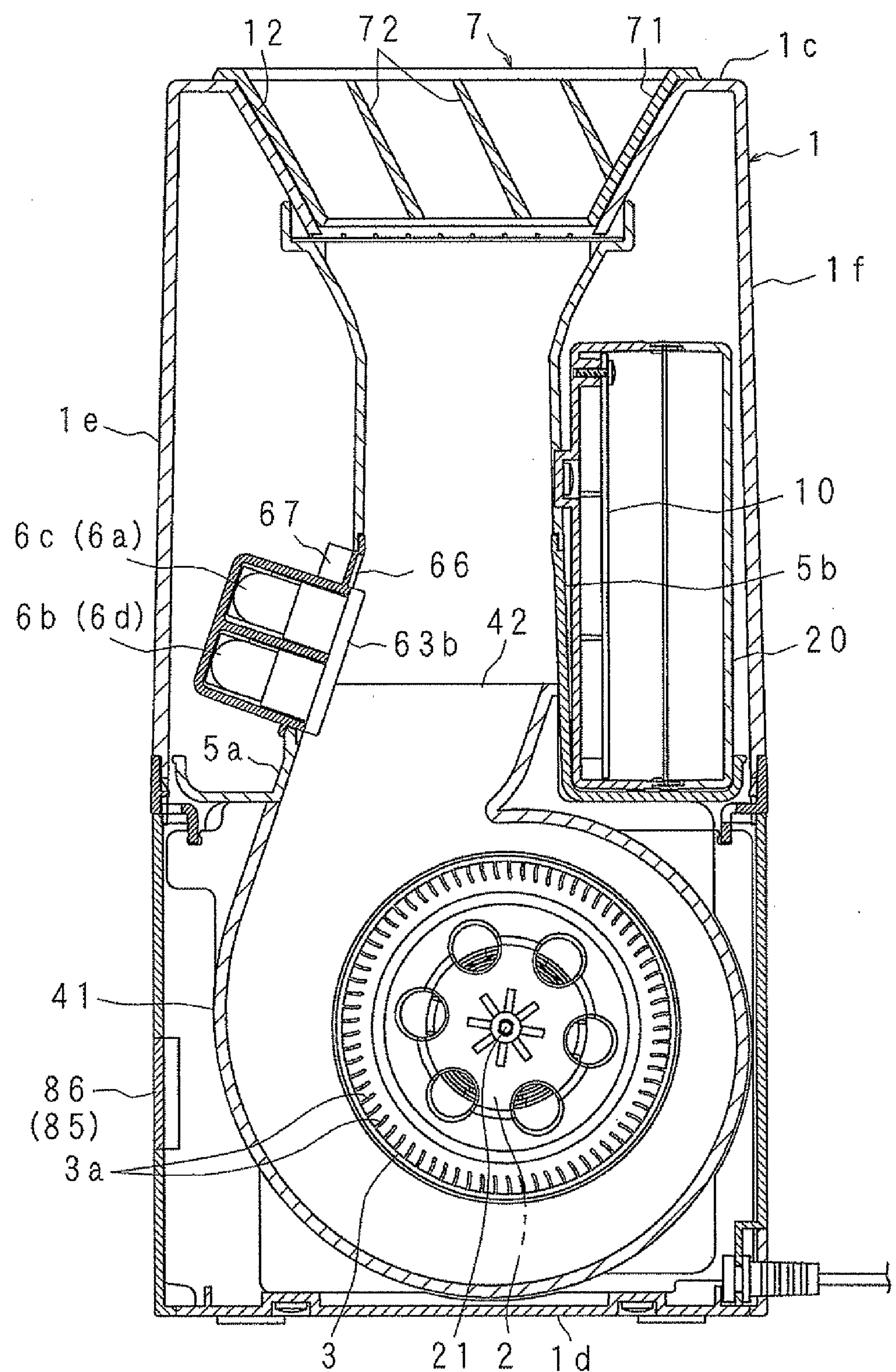
FIG. 2 is a side sectional view illustrating a configuration of an ion generating apparatus.

FIG. 1 is a front-side sectional view illustrating the configuration of an ion generating apparatus according to the present invention. FIG. 2 is a side sectional view illustrating the configuration of an ion generating apparatus. FIG. 3 is a front-side sectional view illustrating the configuration of an ion generator 6*a*. FIG. 4 is a schematic elevation view in which ion generators 6*a*, 6*b*, 6*c*, and 6*d* attached to a front wall 5*a* are viewed from the inner side of a housing 1. The configuration of the other ion generators 6*b*, 6*c*, and 6*d* is similar to that of the ion generator 6*a*.

Numeral 1 in the figure indicates a housing. The housing 1 inlet openings 11 and 11 in the lower part and that are separated from and opposite to each other; and a top wall 1*c* having two fitting holes 12 and 12 in the center part. In the lower part of the housing 1, a motor 2 is arranged that has output shafts 21 and 21 on both sides of the revolution axis directions. The output shafts 21 and 21 of the motor 2 are provided respectively with two impellers 3 and 3 accommodated in two casings 4 and 4 in a freely revolvable manner.

Above the impellers 3 and 3, two ducts 5 and 5 are respectively arranged that serve as tube parts individually guiding upward the air flows generated by the revolution of the impellers. The ducts 5 and 5 respectively have: ion generators 6*a*, 6*b*, 6*c*, and 6*d* each provided with two ion generating parts 61 and 62 in the lower part; and wind direction bodies 7 and 7 arranged in the fitting holes 12 and 12 in a removable manner. Above the ion generators 6*a* and 6*c*, a collecting electrode 66 collecting the generated ions and a measuring part 67 measuring the potential of the collecting electrode 66 are arranged in such a manner that their longitudinal direction is oriented approximately in the horizontal direction and in the adjacent vicinity of the ion generators 6*a* and 6*c*. Here, the motor 2, the impellers 3 and 3, and the casings 4 and 4 constitute a fan.

The housing 1 further has; a bottom wall 1*d* having a rectangular shape in the plane view; and a front wall 1*e* and a rear wall 1*f* that continue from the two front and rear sides of the bottom wall 1*d*, so that an approximately rectangular parallelepiped is formed. The lower part of the front wall 1*e* is provided with: an operation part 85 for receiving operation to the ion generating apparatus; and a display part 86 constructed from LEDs for displaying information such as a warning and an operating status. The inlet openings 11 and 11 in the lower part of the both side walls 1*a* and 1*b* are provided with filters 8 and 8 that pass the air taken in by the impellers 3 and 3 through the inlet openings 11 and 11 and remove foreign substances in the air so as to generate clean air. Each of the fitting holes 12 and 12 of the top wall 1*c* has a rectangular shape whose longitudinal direction is oriented in the front and rear directions. Then, the inner surface on the front side is inclined forward relative to the vertical direction, and the inner surface on the rear side is inclined rearward relative to the vertical direction. Further, the housing 1 is divided into an upper body and a lower body in the middle of the up and down directions. The lower body is provided with the casings 4 and 4, and the upper body is provided with the ducts 5 and 5.

The impellers 3 and 3 are multi-blade impellers having a plurality of blades 3*a* in which the rotation center side displaces in the rotation direction relative to the rim. In other words, these are sirocco fans having a cylindrical shape. Further, the impellers 3 and 3 have bearing plates at particular ends. The output shafts 21 and 21 of the motor 2 are attached to the shaft holes provided in the center of the bearing plates. Then, the air taken into the cavity of the center part through the opening at the other end is released between the blades 3*a* in the outer periphery part.

The casings 4 and 4 have: arc-shaped guide walls 41 and 41 guiding the air flows generated by the revolution of the impellers 3 and 3 toward the rotation direction of the impellers 3 and 3 so as to enhance the velocities of the air flows; and blow-off ports 42 and 42 opened upward from a part of the arc-shaped guide walls 41 and 41 toward one side of the tangential direction of the arc-shaped guide walls 41 and 41. The blow-off ports 42 and 42 have a rectangular pipe shape protruding from a part of the arc-shaped guide walls 41 and 41 toward one side of the tangential direction of the arc-shaped guide walls 41 and 41 into an inclined direction relative to the vertical direction.

Further, the casings 4 and 4 has a deep dish shape and have: casing bodies 4*a* and 4*a* having releasing parts for the arc-shaped guide walls 41 and 41 and for the blow-off ports 42 and 42; and cover plates 4*b* and 4*b* that have releasing parts corresponding to the openings of the impellers 3 and 3 and that close the opening sides of the casing bodies 4*a* and 4*a*. The opposing sides of the casing bodies 4*a* and 4*a* are integrally linked by a connection wall 43 for partition. Further, ventilation plates 9 and 9 having a plurality of air holes are provided between the releasing parts of the cover plates 4*b* and 4*b* and the filters 8 and 8.

The part of the connection wall 43 corresponding to the motor 2 has a recess depressed toward one casing body 4*a* side. Then, a deep-dish-shaped supporting plate 44 is attached to the edge of the recess. Then, the motor 2 is clamped and held between the recess and the center part of the supporting plate 44 via rubber plates 45 and 45. The output shafts 21 and 21 are inserted through the shaft holes provided in the recess and the center part of the supporting plate 44. Then, the impellers 3 and 3 are attached to the output shafts 21 and 21. Further, the upper end of the connection wall 43 extends above the casings 4 and 4.

The ducts 5 and 5 are composed of tube parts having rectangular pipe shapes whose lower ends continue to the blow-off ports 42 and 42, whose upper ends continue to the fitting holes 12 and 12, and whose middle parts in the up and down directions are squeezed. Further, the ducts 5 and 5 have: front walls 5*a* and 5*a* arranged along one side of the tangential direction of the arc-shaped guide surfaces 41 and 41 from the blow-off ports 42 and 42; and rear walls 5*b* and 5*b* arranged almost perpendicularly from the blow-off ports 42 and 42. The front walls 5*a* and 5*a* and the rear walls 5*b* and 5*b* continue to two side walls 5*c*, 5*c*, 5*d*, and 5*d* arranged almost perpendicularly. Then, the air blown off from the blow-off ports 42 and 42 is brought into laminar flows along the front walls 5*a* and 5*a* and the side walls 5*c*, 5*c*, 5*d*, and 5*d* and then guided along the vertical direction.

The front walls 5*a* and 5*a* are provided with a through hole corresponding to a supporting body 63*b* having the ion generators 6*a*, 6*b*, 6*c*, and 6*d*, the collecting electrode 66, and the measuring part 67. Then, the supporting body 63*b* is attached and fit into the through hole. The rear walls 5*b* and 5*b* are provided with: a circuit board 10 connected to the motor 2, the ion generators 6*a*, 6*b*, 6*c*, and 6*d*, the measuring part 67, and a power line; and a cover 20 covering the circuit board 10.

Further, the ducts 5 and 5 are divided into a duct upper body 51 and a duct lower body 52 in the middle of the up and down directions. The duct lower body 52 has a rectangular pipe shape, and the center in the horizontal direction is divided by the connection wall 43. The duct upper body 51 is formed such that the lower parts of square pipe parts 51*a* and 51*a* arranged in parallel in a separated manner in the horizontal direction are integrated by a linkage part 51*b*. Thus, the duct upper body 51 is divided by the linkage part 51*b* and the connection wall 43. Further, the upper end of the duct upper body 51 is provided with protection meshes 30 and 30 avoiding a situation that foreign substances such as a finger are inserted from the outside.

The wind direction bodies 7 and 7 have: rectangular frame parts 71 and 71 whose cross section in the front and rear directions has an inverted trapezium shape; and a plurality of wind direction boards 72 and 72 arranged in parallel in a separated manner in the front and rear directions in the rectangular frame part 71 and 71 and inclined toward one side of the front and rear directions relative to the vertical direction. These wind direction bodies have an identical shape to each other. The front and rear walls of the rectangular frame parts 71 and 71 inclined toward the front and rear directions relative to the vertical direction.

Each of the ion generators 6*a*, 6*b*, 6*c*, and 6*d* is accommodated in a case 60 having an approximately rectangular parallelepiped shape, and has two ion generating parts 61 and 62 arranged in parallel in a separated manner in a direction approximately perpendicular to the direction of flow of the air generated by the revolution of the impellers 3 and 3. Each of the ion generating parts 61 and 62 has: discharge electrodes 61*a* and 62*a* arranged on the electrode substrate 63 and having an acute shape; and dielectric electrodes 61*b* and 62*b* surrounding the discharge electrodes 61*a* and 62*a*. Then, each of the discharge electrodes 61*a* and 62*a* on which a high voltage is applied generates corona discharge. Thus, one ion generating part 61 generates positive ions and the other ion generating part 62 generates negative ions toward the opening side of each of the dielectric electrodes 61*b* and 62*b*.

The electrode substrate 63 is opposite to a circuit board 64 provided with circuit elements such as transistors and resistors. The circuit board 64 has a step-up transformer 65 generating the high voltage, on the side opposite to the negative ion generating part 62. The direction of winding of the coil of the step-up transformer 65 is such that the magnetic flux leaked from the coil is approximately in parallel to the direction of parallel installation of the ion generating parts 61 and 62, in the vicinity of the ion generating part 62 (illustrated by a dashed line in FIG. 3). Synthetic resin is filled in between the electrode substrate 63 and the circuit board 64 and in the surroundings of the step-up transformer 65.

The ion generators 6*a*, 6*b*, 6*c*, and 6*d* are held by the supporting body 63*b* and attached to the front walls 5*a* and 5*a* of the ducts 5 and 5, respectively. The two of the ion generators 6*a* and 6*c* and the ion generators 6*b* and 6*d* are respectively arranged in alignment in the direction of parallel installation in such a manner that the directions of parallel installation of the ion generating parts 61 and 62 are the same. Further, the arrangement is such that the direction of aligned installation and the direction of air flow are approximately perpendicular to each other. The ion generators 6*a* and 6*c* and the ion generators 6*b* and 6*d* are arranged in parallel in the direction of air flow such that the directions of parallel installation of the ion generating parts 61 and 62 are reversed. The ion generating parts 61 and 62 of each of the ion generators 6*a*, 6*b*, 6*c*, and 6*d* face the inside of the ducts 5 and 5 from the through hole. The supporting body 63*b* on both sides of the ion generating parts 61 and 62 continuing in the direction of air flow is provided with ribs 64*a* and 64*a* preventing the user from directly touching the discharge electrodes 61*a* and 62*a*.

The collecting electrode 66 is composed of a plate-shaped electrode having an approximately rectangular shape and collecting ions. Then, in order that negative and positive ions generated respectively by the ion generating part 62 of the ion generator 6*a* and the ion generating part 61 of the ion generator 6*c* should be detected reliably, the collecting electrode 66 is arranged immediately near the ion generating parts 62 and 61 such that the electrode surface is exposed inside the ducts 5 and 5. The electrode surface of the collecting electrode 66 is approximately in parallel to the direction of aligned installation of the ion generators 6*a* and 6*c*. When the collecting electrode 66 collects positive (or negative) ions, the potential of the collecting electrode 66 rises (or falls). The potential of the collecting electrode 66 is measured as a voltage value relative to the ground potential by the measuring part 67 described later.

Here, the collecting electrode 66 has been arranged immediately near the ion generating part 62 of the ion generator 6*a* and the ion generating part 61 of the ion generator 6*c*. However, employable configurations are not limited to this. The collecting electrode 66 may be arranged, for example, in an arbitrary site on the inner surface of the fitting hole 12, or alternatively in an arbitrary site on the side walls 1*a* and 1*b*, the top wall 1*c*, the front wall 1*e*, or the rear wall 1*f* of the housing 1.

The ion generating apparatus constructed as described above is installed in a room of a residence. When the motor 2 of the fan is driven, the impellers 3 and 3 revolve. Then, room air is taken into the two casings 4 and 4 through the inlet openings 11 and 11 on both sides. Foreign substances such as dust in the air taken in are removed by the filters 8 and 8. At that time, the air taken into the casings 4 and 4 is brought into laminar flows by the arc-shaped guide walls 42 and 42 of the circumference of the impellers 3 and 3. Then, the air of laminar flow is guided along the arc-shaped guide walls 41 and 41 to the blow-off ports 42 and 42, and then blown off from the blow-off ports 42 and 42 into the ducts 5 and 5.

FIG. 5 is a block diagram illustrating a schematic configuration of a control system of the ion generating apparatus. A CPU 81 serves the center of the control system. The CPU 81 is connected through a bus to: a ROM 82 storing information such as a program; a RAM 83 storing information generated temporarily; and a timer 84 measuring time. In accordance with a control program stored in advance in the ROM 82, the CPU 81 executes processing such as input/output and arithmetic operations.

The CPU 81 is further connected through a bus to: an operation part 85 receiving the operation of changing the air flow rate of the ion generating apparatus; a display part (means for generating a warning) 86 constructed from LEDs displaying information such as a warning and an operating status; a fan drive circuit 87 driving the motor 2 provided with the impellers 3 and 3; and an A/D conversion circuit 89 converting into a digital voltage the analog voltage measured by the measuring part 67 measuring the potential of the collecting electrode 66, for the purpose of acquisition. The operation part 85 is provided with a buzzer generating an alarm tone (means for generating a warning).

Here, the collecting electrode 66 and the measuring part 67 constitute the ion detector.

The output terminals of the output interfaces 88, 88, 88, and 88 connected to the CPU 81 through the bus are connected to the control inputs PC1, PC2, PC3, and PC4 of the ion generator drive circuits 91, 91, 91, and 91 each having two output terminals. One end of the output terminal of each of the ion generator drive circuits 91, 91, 91, and 91 is connected to the anode of a DC power supply E1 of 14 V whose cathode is connected to the ground inputs G1, G2, G3, and G4 of the respective ion generators 6*a*, 6*b*, 6*c*, and 6*d* and to the ground potential. The other end is connected to the power supply inputs V1, V2, V3, and V4 of the respective ion generators 6*a*, 6*b*, 6*c*, and 6*d*.

When the ion generating apparatus is in an ordinary operating state, at each time that the timer 84 counts a given time, the CPU 81 reverses (switches) the ON/OFF of the control inputs PC1, PC2, PC3, and PC4 of the respective ion generator drive circuits 91, 91, 91, and 91 via the output interfaces 88, 88, 88, and 88. Thus, the ion generator drive circuits 91, 91, 91, and 91 respectively close/open the connection between the power supply inputs V1, V2, V3, and V4 of the ion generators 6*a*, 6*b*, 6*c*, and 6*d* and the anode of the DC power supply E1 for every given time.

Figure 6:
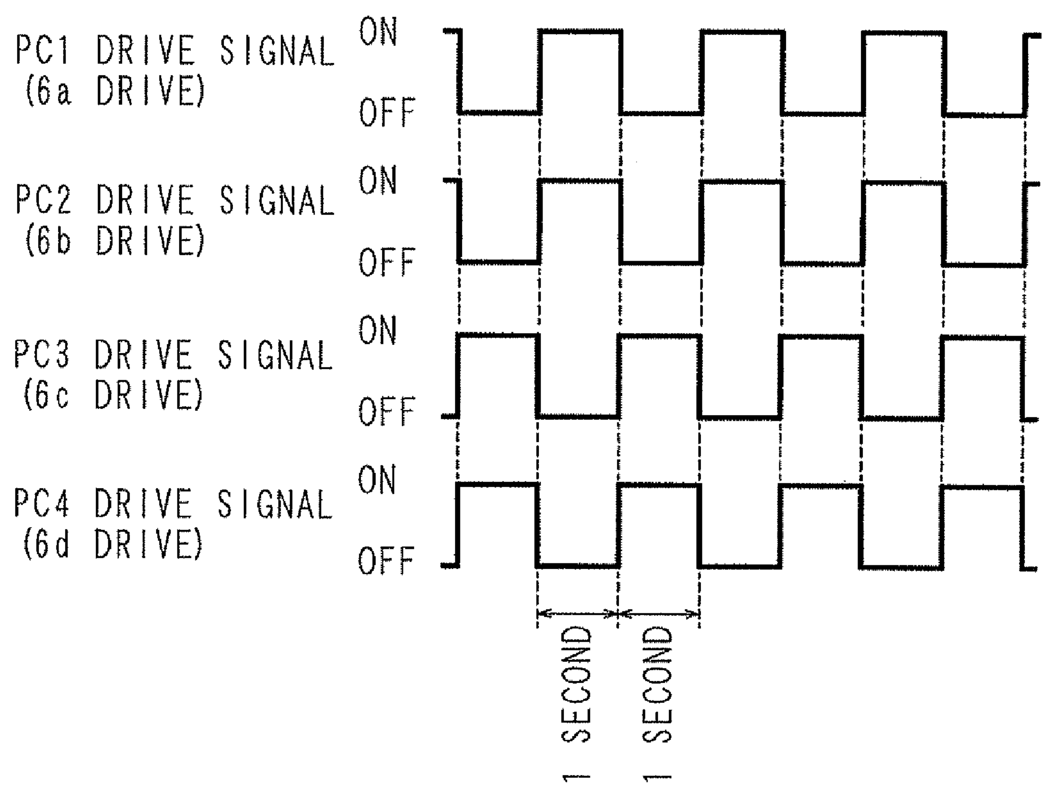
FIG. 6 is a timing chart illustrating drive signals inputted to control inputs in a case that an ion generating apparatus is in an ordinary operating state.

FIG. 6 is a timing chart illustrating drive signals inputted to the control inputs PC1, PC2, PC3, and PC4 in a case that the ion generating apparatus is in an ordinary operating state. The horizontal axis in the figure indicates time (second). The vertical axis indicates the state of ON/OFF. In the drive signals inputted to the control inputs PC1 and PC3, 1-second ON/1-second OFF is repeated alternately with a duty of 50%. In the drive signals respectively inputted to two of the control inputs PC1 and PC2 and the control inputs PC3 and PC4, ON/OFF is repeated in the same phase. Thus, the ion generator drive circuits 91, 91, 91, and 91 close/open the power supply to the ion generators 6*a* and 6*b* and the ion generators 6*c* and 6*d* alternately every other second. Thus, the ion generators 6*a* and 6*b* and the ion generators 6*c* and 6*d* are driven alternately every other second.

FIG. 7 is a circuit diagram illustrating the configuration of the ion detector. The ion detector has the measuring part 67 and the collecting electrode 66 respectively arranged on the component side (the front face) and the detection side (the rear face) of the circuit board.

The measuring part 67 has a resistor R4 pulling up the to collecting electrode 66 to the DC power supply of 5 V. The two terminals of the resistor R4 are connected in parallel to a capacitor C1. The collecting electrode 66 is connected through a protective resistance R1 of the measuring part 67 to the non-inverted input terminal 68 of an operational amplifier IC1 in which a resistor R2 is connected between the inverted input terminal and the output terminal.

The output terminal of the operational amplifier IC1 is connected to resistors R3 and R5 connected in series to each of capacitors C2 and C4 connected to the ground potential. The connection point between the capacitor C2 and the resistor R3 is connected to a protection electrode 69. The connection point between the capacitor C4 and the resistor R5 is connected to the output terminal of the connector CN5. The connector CN5 is used for providing the potential measured by the measuring part 67 to the A/D conversion circuit 89. The protection electrode 69 encloses the surroundings except a part of the collecting electrodes 66, and encloses the protective resistance R1 and the part connected to the two terminals of the protective resistance R1.

In the circuit described above, when the collecting electrode 66 collects positive (or negative) ions, positive charge owned by the positive ions (or negative charge owned by the negative ions) flows into the electrode on the ground side of the capacitor C1 connected to the collecting electrode 66. The potential having risen (or fallen) at the connection point between the capacitor C1 and the protective resistance R1 is provided to the non-inverted input terminal 68 of the operational amplifier IC1 via the protective resistance R1. On the other hand, in the operational amplifier IC1, the output terminal is fed to the inverted input terminal so that an impedance transformer of unity gain (amplification degree 1) is formed. Thus, the potential of the output terminal becomes the same as the potential provided to the non-inverted input terminal 68. This potential is outputted as an analog voltage value relative to the ground potential, through the output terminal of the connector CN5 via the resistor R5.

Further, the output impedance of the operational amplifier IC1 is sufficiently small in comparison with the resistance of the resistor R3. Thus, the protection electrode 69 is maintained at the same potential as the collecting electrode 66 via the resistor R3 (10 kΩ) having 1/100,000 of the resistance of the resistor R4 (1 GΩ) pulling up the collecting electrode 66. Thus, a situation is suppressed that the charge owned by the ions collected by the collecting electrode 66 is conducted along the surface of the circuit board from the collecting electrode 66 to the operational amplifier IC1 so as to move to the outside of the surroundings of the protection electrode 69.

Here, employable constructions of the protective resistance R1 are not limited to a resistor. A series parallel circuit of circuit elements such as resistors and coils may be employed, for example, for a purpose other than protection.

FIGS. 8A and 8B are plan views illustrating a conductor pattern of the circuit board of the ion detector. FIG. 8A illustrates a conductor pattern on the front face on which circuit elements are mounted. FIG. 8B illustrates a conductor pattern on the rear face on which the collecting electrode 66 and the protection electrode 69 are formed. The collecting electrode 66 is electrically connected to the conductor pattern on the front face via the through holes 66*a* and 66*b*. To the conductor pattern, particular sides of the terminals of the protective resistance R1, the resistor R4, and the capacitor C1 are attached.

The protection electrode 69 enclosing the collecting electrode 66 on the rear side has an approximate U-shape in a plane view, where an omitted part K is formed in one side of the longitudinal direction of the circuit board having an approximately rectangular shape. Then, the protection electrode 69 is electrically connected via the through holes 69*a* and 69*b* to the protection electrode 69 enclosing the surroundings of the circuit elements on the front face. The protection electrode 69 on the front face further encloses the conductor pattern and the conductor pattern connecting the protective resistance R1 and the non-inverted input 68.

The plane formed by the protection electrode 69 enclosing the conductor pattern and the protective resistance R1 described above is approximately in parallel to the plane formed by the collecting electrode 66. This minimizes the crossing of the magnetic flux leaked from the step-up transformer 65 with the protection electrode 69.

Figure 9:
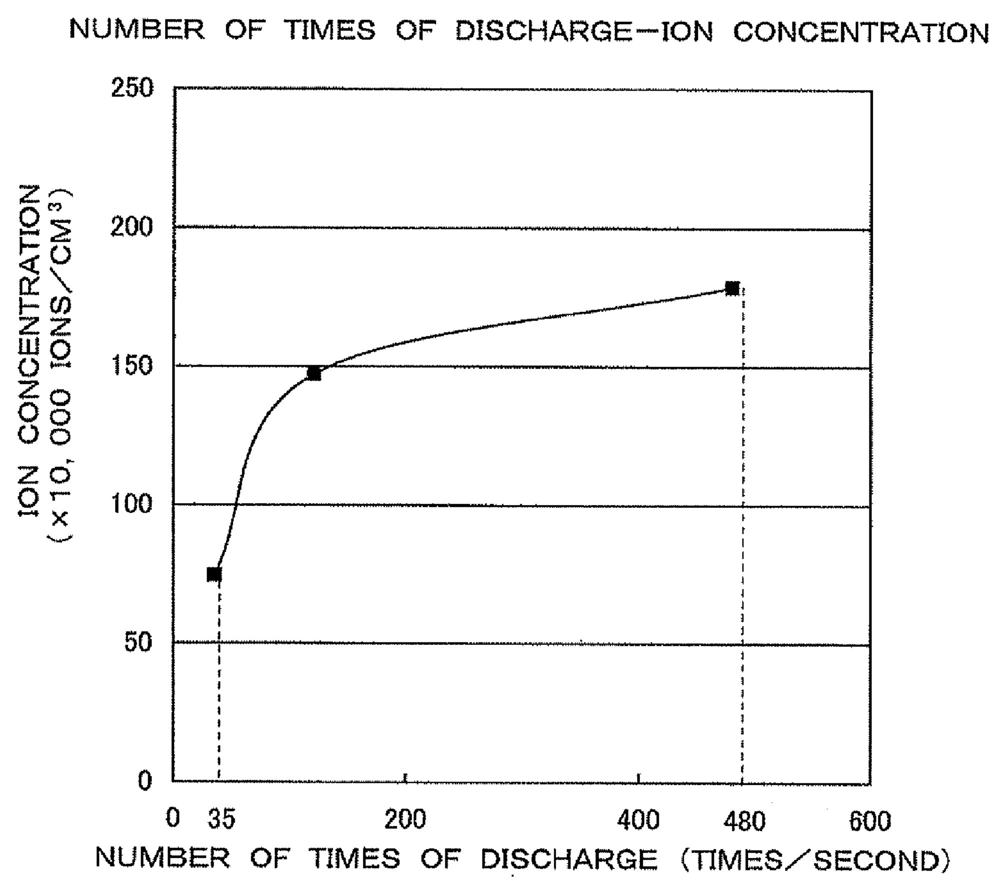
FIG. 9 is a graph expressing the negative ion concentration as a function of the number of times of discharge of an ion generator.

FIG. 9 is a graph expressing the negative ion concentration as a function of the number of times of discharge of the ion generator 6*a* (6*b*, 6*c*, or 6*d*). The horizontal axis in the figure indicates the number of times of discharge per unit time (times/second). The vertical axis indicates the negative ion concentration (×10,000 ions/$cm^3$) measured at a position located at 25 cm above the upper face of the wind direction body 7 releasing ions together with air. When the number of times of discharge is at a standard value of 480 times/second, the ion concentration is approximately 1,800,000 ions/$cm^3$. When the number of times of discharge is, for example, 35 times, the ion concentration is at a value slightly exceeding a half of 1,800,000 ions/$cm^3$. Here, it is recognized that the ion concentration is reduced into a half at the above-mentioned value of 35 times. Then, a threshold value for the judgment of the presence or absence of ions is determined such that the limit of concluding the presence of ions is placed when the number of times of discharge of the ion generator 6*a* is 35 times.

FIGS. 10A and B are graphs expressing the output voltage of the measuring part 67 in a case that the ion generators 6*a* and 6*b* without the rib 64 are turned ON/OFF at an ordinary temperature and an ordinary humidity. This output voltage corresponds to the index detected by the ion detector. The horizontal axis in the figure indicates time (second). The vertical axis indicates the voltage (V). The number of times of discharge is 35 times/second. Here, the collecting electrode 66 of the measuring part 67 collects mainly negative ions generated by the negative ion generating part 62 of the ion generator 6*a*. As illustrated in FIG. 10A, when the ion generators 6*a* and 6*b* are turned ON, the output voltage of the measuring part 67 which has been approximately 5 V falls to approximately 3 V in approximately 5 seconds and then becomes saturated. Further, as illustrated in FIG. 10B, when the ion generators 6*a* and 6*b* are turned OFF, the output voltage of the measuring part 67 which has been approximately 3 V rises to approximately 5 V in approximately 6 seconds and then becomes saturated. Thus, when the ion generators 6*a* and 6*b* are turned ON/OFF, the amount of change in the output voltage of the measuring part 67 is approximately 2 V.

In contrast, it has been recognized by an experiment performed by the present inventors that when the rib 64 is added to the ion generators 6*a* and 6*b*, the amount of change is halved into approximately 1V and that the time elapsing until the saturation of the amount of change becomes 9 seconds or longer. It is unpreferable to that the time necessary in judgment of the presence or absence of ions is extended. Thus, it is preferable that the threshold value for the judgment of the amount of change is reduced further to a value lower than 1V so that a margin is provided.

From these considerations, in the setup of the present embodiment, the ion generators 6*a* and 6*b* are turned ON/OFF every 10 seconds. Then, when the amount of change in the output voltage of the measuring part 67 measured immediately before the ON/OFF switching is greater than 0.5 V, the presence of ions is concluded. This judgment (referred to as ion judgment 1, hereinafter) is intended to judgment at an ordinary temperature and an ordinary humidity. Here, the above-mentioned time of 10 seconds is not limited to this value, and may be longer (or shorter) than 10 seconds.

On the other hand, under the environment of high humidity, the output voltage of the measuring part 67 obtained when the ion generators 6*a* and 6*b* are turned ON/OFF does not fall sufficiently from 5 V (that is, the amount of change in the output voltage at the time of ON/OFF is reduced), and hence a problem arises that judgment of the presence or absence of ions is not achieved satisfactorily. Thus, the present inventors have focused attention on the difference in the output voltage of the measuring part obtained in a case that the ion generators 6*a* and 6*c* installed in alignment in the direction of parallel installation of the ion generating parts 61 and 62 are alternately turned ON/OFF and that the collecting electrode 66 alternately collects negative and positive ions. As a result, it has been found that this difference becomes larger than the above-mentioned amount of change in the output voltage especially under the environment of high humidity.

FIG. 11 is a graph describing a situation that a difference in the amount of change in the output voltage of the measuring part 67 arises owing to a difference in the driving timing of the ion generators. The horizontal axis in the figure indicates the number of times of discharge (time/second) of each ion generator which is driven. The vertical axis indicates the maximum value (V) of the amount of change in the output voltage of the measuring part 67. The solid line indicates a case that the ion generators 6*a* and 6*b* are simultaneously turned ON/OFF every 10 seconds. The dot line indicates a case that the ion generators 6*a* and 6*c* are alternately turned ON/OFF every 10 seconds. As for the environmental conditions, the ambient temperature is 30° C. and the humidity is 95% for all cases.

Even under such an environment that when the ion generators 6*a* and 6*b* are simultaneously turned ON/OFF, the output voltage of the measuring part 67 hardly varies, a tendency is seen that when the ion generators 6*a* and 6*c* are alternately turned ON/OFF, the amount of change in the output voltage of the measuring part 67 (the difference obtained at the time of alternate ON, in this case) increases with increasing number of times of discharge.

Figure 12:
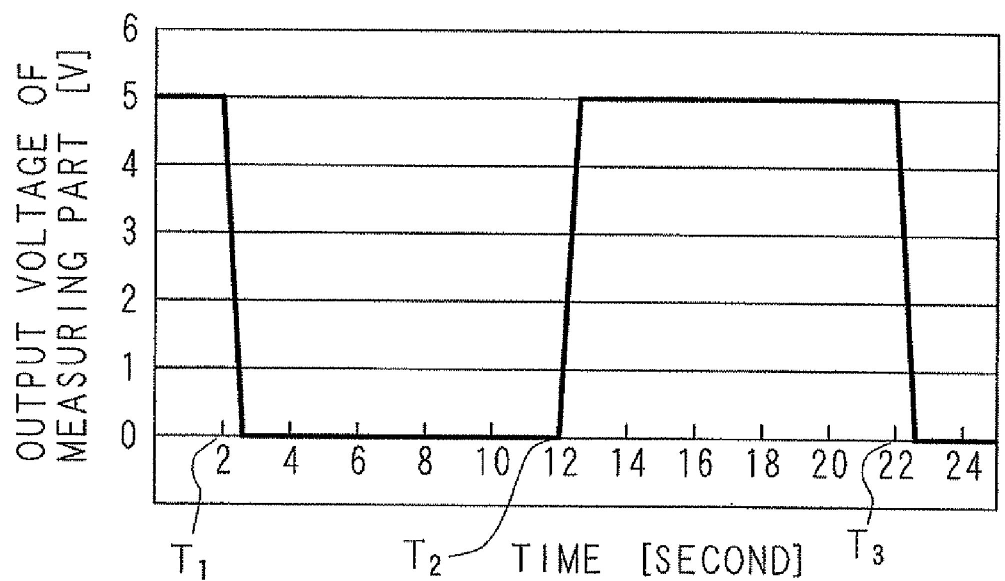
FIG. 12 is a graph expressing the output voltage of a measuring part in a case that an ion generator and an ion generator are alternately turned ON/OFF every 10 seconds at an ordinary temperature and an ordinary humidity.

FIG. 12 is a graph expressing the output voltage of the measuring part 67 in a case that the ion generators 6*a* and 6*b* and the ion generators 6*c* and 6*d* are alternately turned ON/OFF every 10 seconds at an ordinary temperature and an ordinary humidity. The horizontal axis in the figure indicates time (second). The vertical axis indicates the voltage (V). The number of times of discharge is 480 times/second. Here, at times T1 and T3, the ion generators 6*a* and 6*b* are turned ON and the ion generators 6*c* and 6*d* are turned OFF. At time T2, the ion generators 6*a* and 6*b* are turned OFF and the ion generators 6*c* and 6*d* are turned ON. Thus, the collecting electrode 66 of the measuring part 67 alternately collects mainly negative ions generated by the negative ion generating part 62 of the ion generator 6*a* and positive ions generated by the positive ion generating part 61 of the ion generator 6*c*. Here, it is found that even in a case illustrated in FIG. 10 where the ion generators 6*c* and 6*d* are not turned ON/OFF, the waveform of the output voltage of the measuring part 67 varies remarkably from +5 V to almost the ground potential as illustrated in FIG. 12 when the number of times of discharge is set to be 480 times.

Meanwhile, under the environment of high humidity, as described above, the output voltage of the measuring part 67 does not fall sufficiently from +5 V. Even in this case, it has been found by an experiment performed by the present inventors that when the ion generators 6*a* and 6*b* and the ion generators 6*c* and 6*d* are alternately turned ON/OFF, the output voltage of the measuring part 67 once falls steeply immediately after the ion generators 6*a* and 6*b* are turned ON. Thus, when this fall in the output voltage is detected, judgment of the presence or absence of ions is achieved even under the environment of high humidity.

Figure 13:
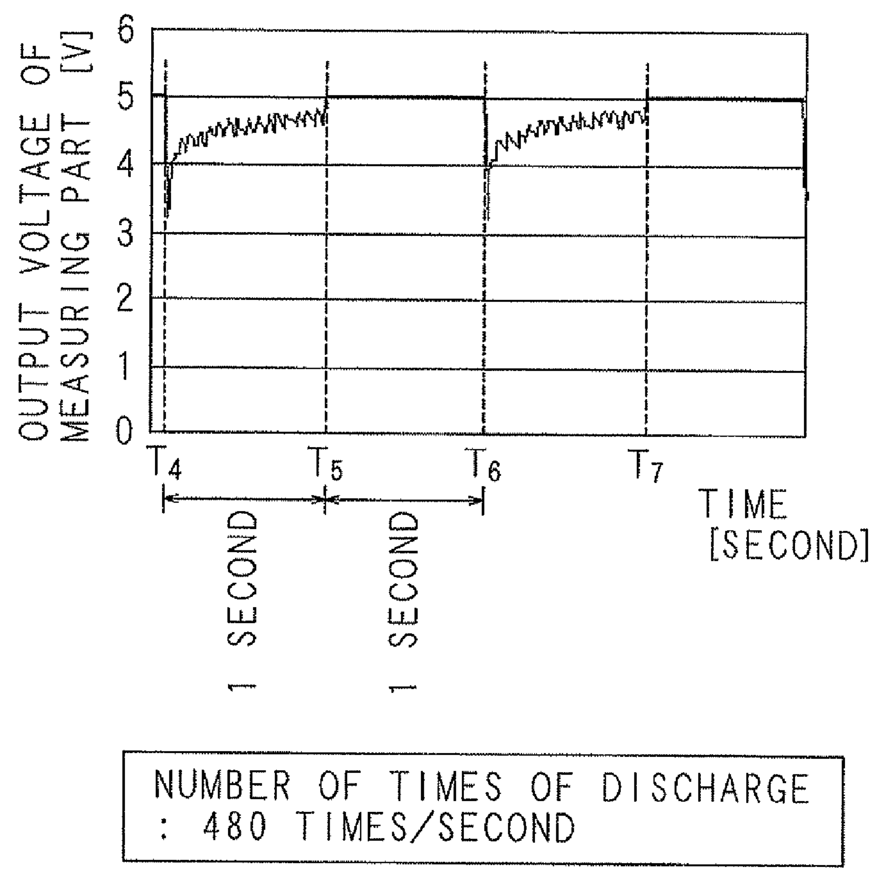
FIG. 13 is a graph expressing the output voltage of a measuring part in a case that an ion generator and an ion generator are alternately turned ON/OFF every second at an ordinary temperature and a high humidity (90% or higher).

FIG. 13 is a graph expressing the output voltage of the measuring part 67 in a case that the ion generators 6*a* and 6*b* and the ion generators 6*c* and 6*d* are alternately turned ON/OFF every 1 second at an ordinary temperature and a high humidity (90% or higher). The horizontal axis in the figure indicates time (second). The vertical axis indicates the voltage (V). The number of times of discharge is 480 times/second. Here, at times T4 and T6, the ion generators 6*a* and 6*b* are turned ON and the ion generators 6*c* and 6*d* are turned OFF. At times T5 and T7, the ion generators 6*a* and 6*b* are turned OFF and the ion generators 6*c* and 6*d* are turned ON. It is seen that immediately after the ion generators 6*a* and 6*b* are turned ON at times T4 and T6, the output voltage falls in a waveform having a local minimum near 3 V and having a peak in the negative direction.

From these considerations, a method that the ion generators 6*a* and 6*b* and the ion generators 6*c* and 6*d* are alternately turned ON/OFF every 1 second and that the presence or absence of ions is judged on the basis of the amount of change to the local minimum of the output voltage immediately after the turn-ON with reference to the output voltage of the measuring part 67 obtained immediately before the ion generators 6*a* and 6*b* are turned ON is referred to as ion judgment 2. Even in a case that judgment of the presence or absence of ions is not achieved satisfactorily by ion judgment 1 described above, ion judgment 2 permits judgment of the presence or absence of ions with precision in a wide range of environment from ordinary temperature and ordinary humidity to high humidity.

Here, in ion judgment 2, the ON/OFF of each ion generator is switched every second with a period of 2 seconds. However, employable configurations are not limited to this. For example, the switching may be performed with a time interval longer than 1 second.

Figure 14:
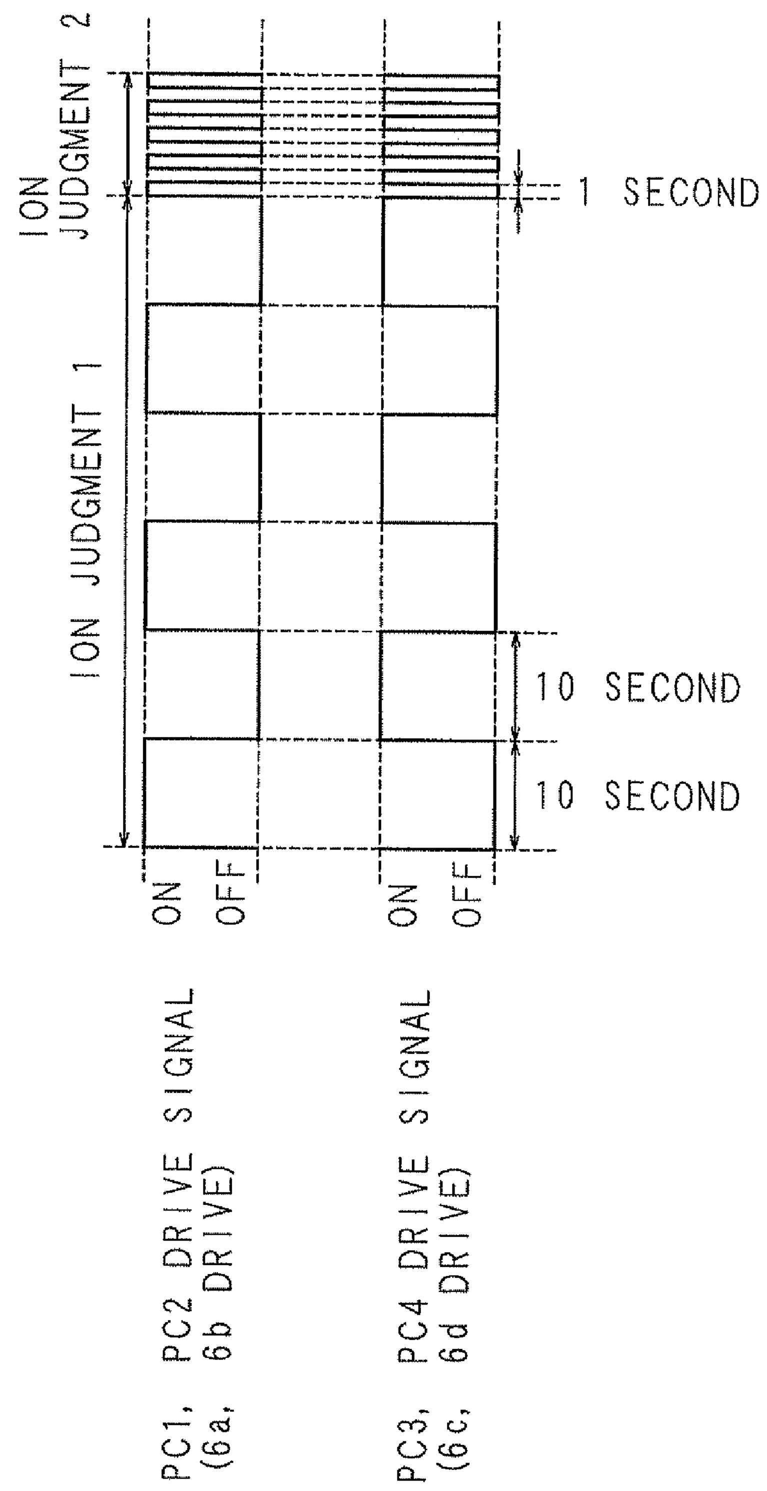
FIG. 14 is a timing chart illustrating drive signals inputted to control inputs when the presence or absence of ions is to be judged.

FIG. 14 is a timing chart illustrating drive signals inputted to the control inputs PC1, PC2, PC3, and PC4 when the presence or absence of ions is to be judged. The horizontal axis in the figure indicates time (second). The vertical axis indicates the state of ON/OFF of the drive signal. In ion judgment 1, the ON/OFF of each drive signal is switched 6 times with a period of 10 seconds. Then, when the presence of ions is concluded, the judgment is normally terminated at the time. When the presence of ions is not concluded, the procedure goes to ion judgment 2 and then the ON/OFF of each drive signal is switched 10 times with a period of 1 second. Then, when the presence of ions is concluded, the judgment is normally terminated at the time. When the presence of ions is not concluded in both of ion judgments 1 and 2, the absence of ions is concluded and then a given count value is counted up. As a result of the judgment of the presence or absence of ions performed every 3 hours, when the above-mentioned count value reaches a given value, a given warning is generated.

In each cycle of ion judgment 1, first, the drive signals to be inputted to the control inputs PC1 and PC2 are turned ON and the drive signals to be inputted to the control inputs PC3 and PC4 are turned OFF. Then, after 10 seconds, the ON/OFF of these drive signals is switched. Then, after another 10 seconds, one cycle is completed. Thus, in the former 10 seconds, only the ion generators 6*a* and 6*b* are ON and hence negative charge generated by the negative ions generated by the ion generating parts 62 is accumulated in the collecting electrode 66. In the next 10 seconds, only the ion generators 6*c* and 6*d* are ON and hence positive charge generated by the positive ions generated by the ion generating parts 61 neutralizes the negative ions accumulated in the collecting electrode 66. Thus, the output voltage of the measuring part 67 falls toward the ground potential in the former half of the 20 seconds and rises toward the supply voltage of the DC power supply (5 V) in the latter half (see FIG. 12).

When the presence or absence of ions is judged in ion judgment 1, the presence of ions is concluded in a case that the difference between the maximum value and the minimum value of the output voltage during the period of ion judgment 1 is greater than a given voltage (i.e., 0.5 V).

The only difference in the drive signals inputted to the control inputs PC1 to PC4 in each cycle of ion judgment 2 is that the period (2 seconds) of ON/OFF of each drive signal is different from the period (20 seconds) in ion judgment 1.

When the presence or absence of ions is judged in ion judgment 2, the presence of ions is concluded in a case that the difference between the maximum value and the minimum value of the output voltage during the period of ion judgment 2 is greater than a given voltage (i.e., 0.5 V).

The operation of the ion generating apparatus having the above-mentioned configuration is described below with reference to a flow chart describing the operation.

FIG. 15 is a flow chart illustrating a processing procedure of the CPU 81 driving the ion generators 6*a*, 6*b*, 6*c*, and 6*d* in an ordinary operating state. FIG. 16 is a flow chart illustrating a processing procedure of the CPU 81 concerning a subroutine for switching of the PCs 1 to 4. The processing of FIGS. 15 and 16 is executed in accordance with a control program stored in advance in the ROM 82. Further, the processing of FIG. 15 is re-executed at each time that the processing is completed.

Here, a "measurement flag" indicating that the measurement for judging the presence or absence of ions is on-going and a "toggle flag" indicating the phase of ON/OFF are stored in the RAM 83.

When the processing of FIG. 15 is started, the CPU 81 causes the timer 84 to start the time counting of 1 second (step S11). Here, the time to be counted is not limited to 1 second. For example, a time length such as 0.5 second and 1.5 seconds may be employed. After that, the CPU 81 judges whether the timer 84 has completed the time counting (step S12). When it is concluded that the time counting is not completed (step S12: NO), the CPU 81 waits until the timer 84 completes the time counting.

When it is concluded that the time counting has been completed (step S12: YES), the CPU 81 judges whether the "measurement flag" has been set to be 1 (step S13). When it is concluded that the setting has been done (step S13: YES), the CPU 81 terminates the processing immediately. Thus, during the judgment of the presence or absence of ions, the ion generators 6*a*, 6*b*, 6*c*, and 6*d* are maintained not to be turned ON/OFF in the present processing. When it is concluded that the "measurement flag" has not been set to 1 (step S13: NO), the CPU 81 calls and executes a subroutine concerning the switching of the PCs 1 to 4 (step S14), and then terminates the processing.

When the subroutine concerning the switching of the PCs 1 to 4 illustrated in FIG. 16 is called, the CPU 81 judges whether the "toggle flag" has been set to be 1 (step S21). When it is concluded that the setting has been done (step S21: YES), the CPU 81 clears the "toggle flag" into 0 (step S22), and further turns ON the control input PC1 of the ion generator drive circuit 91 through the output interface 88 (step S23). Similarly, the CPU 81 turns ON the control input PC2 (step S24), turns OFF the control input PC3 (step S25), further turns OFF the control input PC4 (step S26), and then terminates the processing.

When it is concluded that the "toggle flag" has not been set to 1 at step S21 (step S21: NO), the CPU 81 sets the "toggle flag" to 1 (step S27), and further turns OFF the control input PC1 of the ion generator drive circuit 91 through the output interface 88 (step S28). Similarly, the CPU 81 turns OFF the control input PC2 (step S29), turns ON the control input PC3 (step S30), further turns ON the control input PC4 (step S31), and then terminates the processing.

As such, the CPU 81 switches the ON/OFF of the control inputs PC1, PC2, PC3, and PC4 of the ion generator drive circuit 91.

Figure 18:
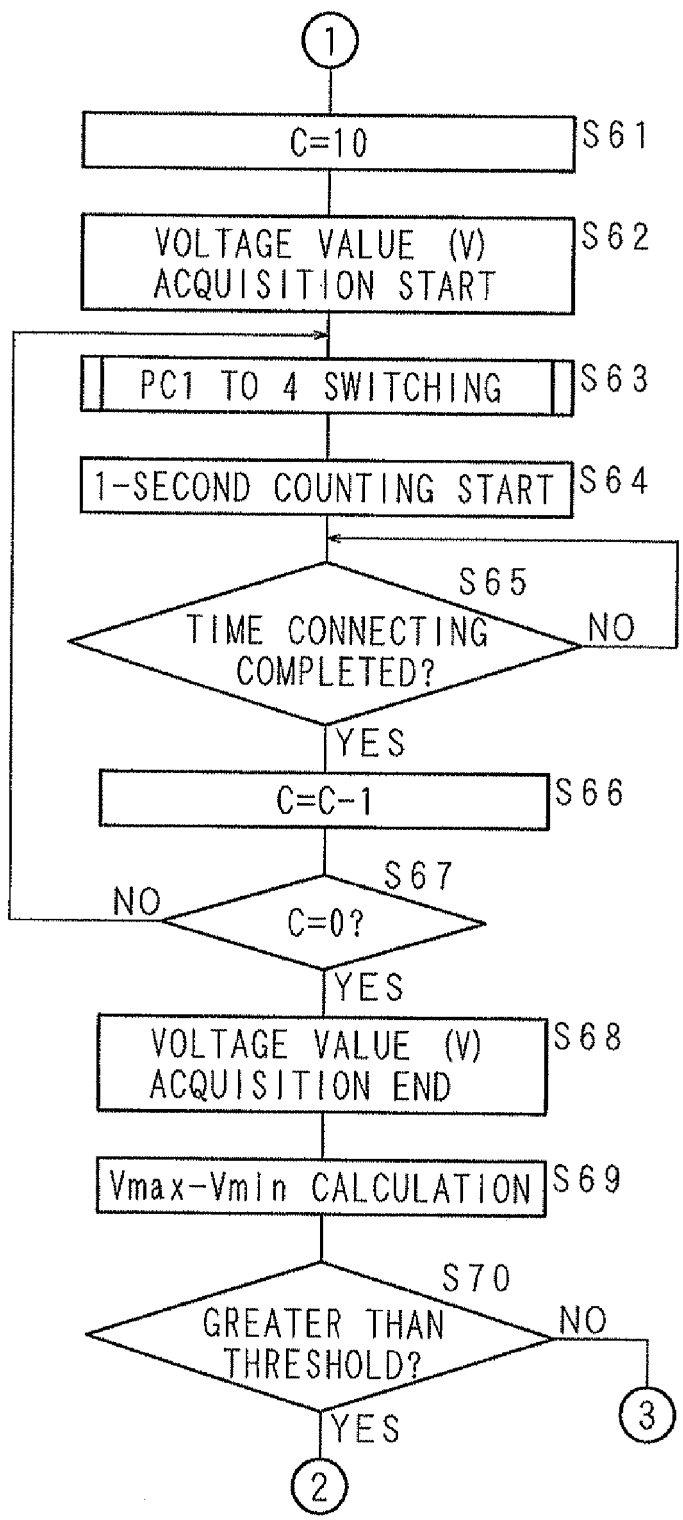
FIG. 18 is a flow chart illustrating a processing procedure of a CPU for generating a warning on the basis of a result of judgment of the presence or absence of ions.
Figure 19:
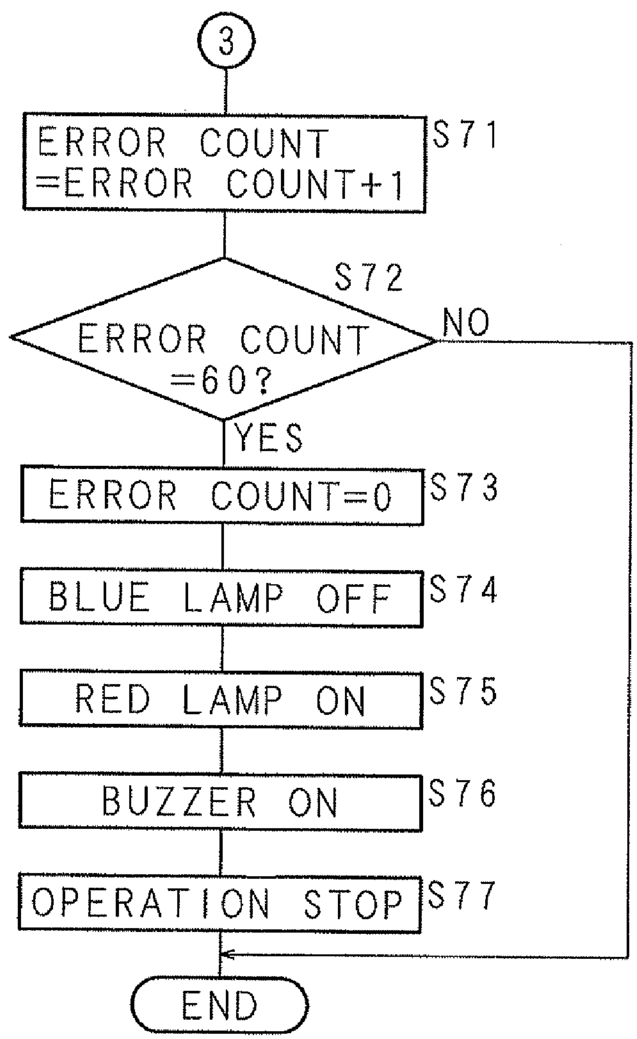
FIG. 19 is a flow chart illustrating a processing procedure of a CPU for generating a warning on the basis of a result of judgment of the presence or absence of ions.

FIGS. 17, 18, and 19 are a flow chart illustrating a processing procedure of the CPU 81 generating a warning on the basis of the result of judgment of the presence or absence of ions. In accordance with a control program stored in advance in the ROM 82, the following processing is executed after 30 seconds of the initialization processing performed by the CPU 81. After that, the present processing is repeated every 3 hours. This repeating cycle is not limited to 3 hours.

Here, the "loop count (C)" and the "error count" are variables stored in the RAM 83. The value of 0 is written into the "error count" in the initialization processing performed by the CPU 81.

When the processing of FIG. 17 is started, the CPU 81 sets the "measurement flag" to be 1 as initialization (step S41), then sets the "toggle flag" to be 1 (step S42), and then substitutes 6 into the "loop count (C)" storing the number of times of switching of the PCs 1 to 4 in ion judgment 1 (step S43). After that, the CPU 81 starts acquisition of the voltage value (V) of the output voltage of the measuring part 67 through the A/D conversion circuit 89 (step S44). Hereinafter, it is assumed that the acquired voltage value (V) is store sequentially into a register of the CPU 81 or into the RAM 83.

Then, the CPU 81 calls and executes a subroutine concerning the switching of the PCs 1 to 4 (step S45), and causes the timer 84 to start time counting for 10 seconds (step S46). After that, the CPU 81 judges whether the timer 84 has completed the time counting (step S47). When it is concluded that the time counting is not completed (step S47: NO), the CPU 81 waits until the timer 84 completes the time counting.

When it is concluded that the time counting has been completed (step S47: YES), the CPU 81 subtracts 1 from the "loop count (C)" (step S48), and judges whether "C" is 0 (step S49). When it is concluded that the value is not 0 (step S49: NO), the CPU 81 returns the processing to step S45. By virtue of this, switching of the PCs 1 to 4 is repeated.

At step S49, when it is concluded that "C" has become 0 (step S49: YES), the CPU 81 terminates the acquisition of the output voltage of the measuring part 67 (step S50). After that, the CPU 81 calculates the difference between the maximum value and the minimum value of the voltage value (V) stored in the register or the RAM 83 (step S51), and judges whether the calculated difference is greater than a given threshold value (0.5 V) (step S52). When it is concluded that the value is greater than the given threshold value (step S52: YES), that is, when the presence of ions is concluded, the CPU 81 clears the "measurement flag" into 0 (step S53) in order to indicate the completion of the judgment of the presence or absence of ions then clears the "error count" into 0 (step S54), and then terminates the processing. As a result, the history of conclusion of the absence of ions is cleared.

At step S52, when it is concluded that the value is smaller than the given threshold value (step S52: NO), that is, when the presence of ions is not concluded, the CPU 81 substitutes 10 into the "loop count (C)" storing the number of times of switching of the PCs 1 to 4 in ion judgment 2 (step S61). Then, the CPU 81 starts acquisition of the voltage value (V) of the output voltage of the measuring part 67 through the A/D conversion circuit 89 (step S62). Hereinafter, it is assumed that the acquired voltage value (V) is stored sequentially into a register of the CPU 81 or into the RAM 83.

Then, the CPU 81 calls and executes a subroutine concerning the switching of the PCs 1 to 4 (step S63), and causes the timer 84 to start time counting for 1 second (step S64). After that, the CPU 81 judges whether the timer 84 has completed the time counting (step S65). When it is concluded that the time counting is not completed (step S65: NO), the CPU 81 waits until the timer 84 completes the time counting.

When it is concluded that the timer 84 has completed the time counting (step S65: YES), the CPU 81 subtracts 1 from the "loop count (C)" (step S66), and judges whether "C" is 0

(step S67). When it is concluded that the value is not 0 (step S67: NO), the CPU 81 returns the processing to step S63.

At step S67, when it is concluded that the "loop count (C)" has become 0 (step S67: YES), the CPU 81 terminates the acquisition of the output voltage of the measuring part 67 (step S68). After that, the CPU 81 calculates the difference between the maximum value and the minimum value of the voltage value (V) stored in the register or the RAM 83 (step S69), and judges whether the calculated difference (the amount of change) is greater than the given threshold value (0.5 V) (step S70). When it is concluded that the value is greater than the given threshold value (step S70: YES), that is, when the presence of ions is concluded, the CPU 81 returns the processing to step S53.

At step S70, when it is concluded that the value is smaller than the given threshold value (0.5V) (step S70: NO), that is, when the presence of ions has been not concluded in both of ion judgment 1 and ion judgment 2, the CPU 81 adds 1 to the "error count" (step S71), and judges whether the "error count" has become 60 (step S72). When it is concluded that the value does not reach 60 (step S72: NO), the CPU 81 terminates the processing.

When it is concluded that the "error count" has become 60 (step S72: YES), that is, when it is concluded that the absence of ions is concluded, the CPU 81 clears the "error count" into 0 (step S73) and, in order to notify the absence of ions, turns OFF a blue lamp in the display part 86 (step S74) and turns ON a red lamp indicating a warning (step S75). As a warning by sound, the CPU 81 operates a buzzer provided in the operation part 85 (step S76), then performs other necessary processing for shutdown (step S77), and then terminates the processing.

Here, the number of times of judgment for the "error count" is not limited to 60, and may be an arbitrary value.

As described above, according to the present embodiment, in a case that ion generators mainly generating positive and negative ions respectively to a collecting electrode are turned ON at different timings, when the difference in the output voltage of a measuring part is greater (or smaller) than 0.5 V, the presence (or the absence) of ions is concluded.

By virtue of this, like in a case that air under the judgment of the presence or absence of ions is at a high temperature and a high humidity or in a case that the rate of ion generation has decreased owing to a time dependent change of the ion generators, even in a case that the amount of change in the output voltage of the measuring part associated with the ON/OFF of one ion generator is small and hence judgment of the presence or absence of ions is difficult, judgment of the presence or absence of ions is achieved without errors. Thus, judgment of the presence or absence of ions is achieved with precision free from the influence of the temperature and the humidity and the influence of a time dependent change in the ion generators.

Further, ion generators in which the directions of parallel installation of positive and negative ion generating parts are made the same are biased such that the overlap in the direction of parallel installation is exactly cleared, and the direction of the air flow running near each ion generating part and the direction of parallel installation are approximately at right angles to each other. Thus, the collecting electrode collects ions generated respectively by the positive ion generating part of one ion generator and the negative ion generating part of the other ion generator.

Thus, the difference in the output voltage of the measuring part obtained when the individual ion generators are turned ON at different timings increases in comparison with the amount of change in the output voltage obtained when one ion generator is turned ON/OFF. Thus, the presence or absence of ions is judged easily.

Further, the ion generators are installed in contact in alignment in the direction of parallel installation of the ion generating parts, and the opening side of each ion generating part is oriented to a direction approximately perpendicular to the direction of aligned installation.

Thus, the separation distance between the collecting electrode and the installed in alignment-ion generators is almost minimized. Thus, the difference in the output voltage of the measuring part in a case that the individual ion generators are turned ON at different timings is almost maximized and hence judgment of the presence or absence of ions is achieved reliably. Further, the ions generated in the ventilation flue by the ion generating part are conducted efficiently together with the air flow in the ventilation flue.

Further, the presence or absence of ions is judged in a state that the ion generators mainly generating positive and negative ions respectively to the collecting electrode are turned ON alternately with a period of 20 seconds (every 10 seconds).

Thus, no overlap occurs between the ON timings in the ion generators. Thus, the difference in the output voltage of the measuring part in a case that the individual ion generators are turned ON at different timings is almost maximized and hence judgment of the presence or absence of ions is achieved reliably. Further, the judgment is performed periodically, that is, the same processing is repeated. This reduces the probability of erroneous conclusion as the absence of ions.

Further, when the absence of ions is concluded in ion judgment 1 performed with a period of 20 seconds, the presence or absence of ions is judged again after the ion generator mainly generating negative ions to the collecting electrode is turned ON with a period of 2 seconds.

Thus, the presence or absence of ions is judged with focusing attention on the amount of change in the output voltage of the measuring part occurring when the one ion generator is turned ON. Accordingly, the presence or absence of ions is judged by recognizing a rapid change in the output voltage occurring when the ions are changed from positive to negative. Thus, like in a case that the humidity of air under the judgment of the presence or absence of ions is extremely high, even in a case that the output voltage of the measuring part having once varied varies to the opposite direction during the time that the ion generator is ON, the presence or absence of ions is judged without errors.

Further, when the absence of ions has been concluded 60 successive times, a warning is generated to the user through an LED of the display part and a buzzer of the operation part.

Thus, when the rate of ion generation falls, the user is notified and prompted to cleaning of the ion generating part or replacement of the ion generator.

Here, in the present embodiment, a red lamp of the display part 86 is turned ON as a warning, and a warning sound is generated from a buzzer. However, employable configurations are not limited to this. For example, a warning voice may be generated by an electronic speech circuit and a speaker.

Further, in ion judgment 1, the difference in the output voltage of the measuring part 67 obtained immediately before the switching of ON/OFF of the ion generators 6*a* and 6*b* and the ion generators 6*c* and 6*d* is compared with a given threshold value. However, employable configurations are not limited to this. For example, the minimum value and the maximum value may respectively be determined for the output voltage of the measuring part sampled for every second during the time that the ion generators 6*a* and 6*b* are turned ON for 10 seconds and turned OFF for 10 seconds. Then, the difference of the determined maximum and minimum values may be compared with a threshold value.

Further, the collecting electrode 66 is pulled up to DC 5 V by a resistor. Then, the presence or absence of ions is judged with focusing attention on the negative ions. However, employable configurations are not limited to this. For example, the electrode may be pulled down to the ground potential by a resistor, and then the presence or absence of ions may be judged with focusing attention on the positive ions.

The invention claimed is:

1. An ion generating apparatus in which a plurality of ion generators generate positive and negative ions, comprising:

a drive circuit turning ON/OFF the ion generators;

an ion detector detecting an index indicating a state of generation of the ions generated by the ion generators; and a judgment part judging presence or absence of the ions on the basis of the index detected by the ion detector, wherein in a case that the drive circuit turns ON one ion generator and the other ion generator periodically at different timings, when a difference of the indices detected by the ions detector is greater than a given threshold value, the judgment part concludes presence of the ions.

2. The ion generating apparatus according to claim 1, wherein in the one ion generator and the other ion generator, positive and negative ion generating parts are installed in parallel in each ion generator, the directions of parallel installation of the individual ion generating parts are aligned, and the ion generators are biased such that the ion generating parts do not overlap in the direction of parallel installation.

3. The ion generating apparatus according to claim 2, wherein the one ion generator and the other ion generator are installed in alignment in the direction of parallel installation, and wherein each ion generating part generates ions toward one side of a direction crossing perpendicularly to the direction of aligned installation.

4. The ion generating apparatus according to claim 1, wherein when the drive circuit turns ON the one ion generator and the other ion generator alternately with a given period, the judgment part judges presence or absence of the ions.

5. The ion generating apparatus according to claim 4, wherein in a case that the judgment part has concluded absence of the ions, the judgment part again judges presence or absence of the ions at the time that the drive circuit turns ON the one ion generator.

6. The ion generating apparatus according to claim 4, comprising a warning part generating a warning when the judgment part has concluded absence of the ions in a given number of successive occasions.

7. A judgment method for presence or absence of ions of judging presence or absence of ions, comprising:

turning ON/OFF a plurality of ion generators so as to generate positive and negative ions;

detecting through an ion detector an index indicating a state of generation of the ions generated by the ion generators; and in a case that the ion generators respectively generating positive and negative ions are turned ON periodically at different timings, when a difference of the indices detected by the ions detector is greater than a given threshold value, concluding presence of the ions.

8. The judgment method for presence or absence of ions according to claim 7, wherein in the one ion generator and the other ion generator, positive and negative ion generating parts are installed in parallel in each ion generator, the directions of parallel installation of the individual ion generating parts are aligned, and the ion generators are biased such that the ion generating parts do not overlap in the direction of parallel installation.

9. The judgment method for presence or absence of ions according to claim 8, wherein the one ion generator and the other ion generator are installed in alignment in the direction of parallel installation, and wherein each ion generating part generates ions toward one side of a direction crossing perpendicularly to the direction of aligned installation.

10. The judgment method for presence or absence of ions according to claim 7, wherein when the drive circuit turns ON the one ion generator and the other ion generator alternately with a given period, presence or absence of the ions is judged.

11. The judgment method for presence or absence of ions according to claim 10, wherein in a case that absence of the ions has been concluded, presence or absence of the ions is judged again at the time that the drive circuit turns ON the one ion generator.

12. The judgment method for presence or absence of ions according to claim 10, wherein when absence of the ions has been concluded in a given number of successive occasions, a warning is generated.

* * * * *